US009495505B2

(12) United States Patent
Perkins et al.

(10) Patent No.: US 9,495,505 B2
(45) Date of Patent: Nov. 15, 2016

(54) ADJUSTING FABRICATION OF INTEGRATED COMPUTATIONAL ELEMENTS

(71) Applicant: Halliburton Energy Services, Inc., Houston, TX (US)

(72) Inventors: David L. Perkins, The Woodlands, TX (US);
(Continued)

(73) Assignee: Halliburton Energy Services, Inc., Houston, TX (US)

(*) Notice: Subject to any disclaimer, the term of this patent is extended or adjusted under 35 U.S.C. 154(b) by 210 days.

(21) Appl. No.: 14/390,971

(22) PCT Filed: Dec. 24, 2013

(86) PCT No.: PCT/US2013/077683
§ 371 (c)(1),
(2) Date: Oct. 6, 2014

(87) PCT Pub. No.: WO2015/099706
PCT Pub. Date: Jul. 2, 2015

(65) Prior Publication Data
US 2016/0196380 A1 Jul. 7, 2016

(51) Int. Cl.
*G06F 17/50* (2006.01)

(52) U.S. Cl.
CPC ....... *G06F 17/5081* (2013.01); *G06F 17/5045* (2013.01)

(58) Field of Classification Search
USPC .......................................................... 716/54
See application file for complete search history.

(56) References Cited

U.S. PATENT DOCUMENTS

| 5,075,550 A | 12/1991 | Miller et al. |
| 5,399,229 A | 3/1995 | Stefani et al. |

(Continued)

FOREIGN PATENT DOCUMENTS

| WO | WO 2004/015364 | 2/2004 |
| WO | WO 2006/031733 | 3/2006 |

(Continued)

OTHER PUBLICATIONS

Extended European Search Report, EP 13885459.1, Nov. 19, 2015, 12 pages.

(Continued)

*Primary Examiner* — Eric Lee
(74) *Attorney, Agent, or Firm* — Benjamin Fite; Parker Justiss, P.C.

(57) ABSTRACT

Techniques include receiving a design of an integrated computational element (ICE) including (1) specification of a substrate and multiple layers, their respective target thicknesses and refractive indices, adjacent layer refractive indices being different from each other, and a notional ICE fabricated based on the ICE design being related to a characteristic of a sample, and (2) indication of target ICE performance; forming one or more of the layers of an ICE based on the ICE design; in response to determining that an ICE performance would not meet the target performance if the ICE having the formed layers were completed based on the received ICE design, updating the ICE design to a new total number of layers and new target layer thicknesses, such that performance of the ICE completed based on the updated ICE design meets the target performance; and forming some of subsequent layers based on the updated ICE design.

28 Claims, 6 Drawing Sheets

(72) Inventors: Robert Paul Freese, Pittsboro, NC (US); Christopher Michael Jones, Houston, TX (US); Richard Neal Gardner, Raleigh, NC (US); James M. Price, The Woodlands, TX (US); Aditya B Nayak, Humble, TX (US)

(56) References Cited

U.S. PATENT DOCUMENTS

| | | |
|---|---|---|
| 5,453,716 A | 9/1995 | Person et al. |
| 5,537,479 A | 7/1996 | Kreisel et al. |
| 5,619,366 A | 4/1997 | Rhoads et al. |
| 6,078,389 A | 6/2000 | Zetter |
| 6,154,550 A | 11/2000 | Beyer |
| 6,163,259 A | 12/2000 | Barsumian et al. |
| 6,198,531 B1 | 3/2001 | Myrick et al. |
| 6,213,250 B1 | 4/2001 | Wisniewski et al. |
| 6,529,276 B1 | 3/2003 | Myrick |
| 6,646,753 B2 | 11/2003 | Zhang et al. |
| 6,804,060 B1 | 10/2004 | Tsai et al. |
| 6,905,578 B1 | 6/2005 | Moslehi et al. |
| 6,965,431 B2 | 11/2005 | Vo-Dinh et al. |
| 7,138,156 B1 * | 11/2006 | Myrick .................. G02B 5/285 359/359 |
| 7,163,901 B2 | 1/2007 | Downey |
| 7,332,044 B2 | 2/2008 | Sidorin et al. |
| 7,679,563 B2 | 3/2010 | Werner et al. |
| 7,697,141 B2 | 4/2010 | Jones et al. |
| 7,753,847 B2 | 7/2010 | Greenleaf et al. |
| 7,777,870 B2 | 8/2010 | Hayes et al. |
| 7,792,644 B2 | 9/2010 | Kotter et al. |
| 7,828,929 B2 | 11/2010 | Lee et al. |
| 7,911,605 B2 | 3/2011 | Myrick et al. |
| 7,920,258 B2 | 4/2011 | Myrick et al. |
| 8,054,212 B1 | 11/2011 | Holly et al. |
| 8,106,850 B1 | 1/2012 | Gregoire et al. |
| 8,164,061 B2 | 4/2012 | Pawlak et al. |
| 8,216,161 B2 | 7/2012 | Darlington et al. |
| 8,252,112 B2 | 8/2012 | Ovshinsky |
| 2005/0054928 A1 | 3/2005 | Cerofolini |
| 2006/0055935 A1 | 3/2006 | Cheben et al. |
| 2007/0100580 A1 | 5/2007 | Marcus et al. |
| 2008/0237492 A1 | 10/2008 | Caliendo et al. |
| 2009/0182693 A1 | 7/2009 | Fulton et al. |
| 2012/0268744 A1 | 10/2012 | Wolf et al. |
| 2013/0284894 A1 | 10/2013 | Freese et al. |
| 2013/0284895 A1 | 10/2013 | Freese et al. |
| 2013/0284896 A1 | 10/2013 | Freese et al. |
| 2013/0284897 A1 | 10/2013 | Freese et al. |
| 2013/0284898 A1 | 10/2013 | Freese et al. |
| 2013/0284899 A1 | 10/2013 | Freese et al. |
| 2013/0284900 A1 | 10/2013 | Freese et al. |
| 2013/0284901 A1 | 10/2013 | Freese et al. |
| 2013/0284904 A1 | 10/2013 | Freese et al. |
| 2013/0286398 A1 | 10/2013 | Freese et al. |
| 2013/0286399 A1 | 10/2013 | Freese et al. |
| 2013/0287061 A1 | 10/2013 | Freese et al. |

FOREIGN PATENT DOCUMENTS

| | | |
|---|---|---|
| WO | WO 2007/015115 | 2/2007 |
| WO | WO 2008/106391 | 9/2008 |
| WO | WO 2011/103066 | 8/2011 |
| WO | WO2012108885 | 8/2012 |
| WO | WO 2013/022556 | 2/2013 |
| WO | WO2015099671 | 7/2015 |

OTHER PUBLICATIONS

Halbach et al., "On-Line Reoptimization of Filter Designs for Multivariate Optical Elements", Optical Society of America, vol. 42, No. 10, Apr. 1, 2003, 6 pages.

International Search Report and Written Opinion of the International Searching Authority issued in International Application No. PCT/US2013/077683 on Sep. 1, 2014; 9 pages.

International Search Report and Written Opinion of the International Searching Authority issued in International Application No. PCT/US2013/077685 on Sep. 1, 2014; 8 pages.

Frey et al., "Temperature-dependent refractive index of silicon and germanium," NASA Goodard Space Flight Center, Greenbelt, MD, 2006, 10 pages.

Morton et al., "Optical Monitoring of Thin-films Using Spectroscopic Ellipsometry," Society of Vacuum Coaters, 45th Annual Technical Conference Proceedings, 2002, 7 pages.

Eastwood et al., "Field applications of stand-off sensing using visible/NIR multivariate optical computing," Department of Chemistry and Biochemistry, University of South Carolina, SPE vol. 4199, 2001, 10 pages.

Paul et al., "Fabrication of mid-infrared frequency-selective surfaces by soft lithography", Applied Optics, v. 40, No. 25, Sep. 2001, 5 pages.

Haibach et al., "Precision in multivariate optical computing," Applied Optics, vol. 43, No. 10, Apr. 1, 2004, 11 pages.

J.A. Woollam Co., Inc., Characterizing Processes with EASE® In Situ Applications, Application Note, 2009, 3 pages.

Li, "Refractive Index of Silicon and Germanium and Its Wavelength and Temperature Derivatives," Center for Information and Numerical Data Analysis and Synthesis, Purdue University, J. Phys. Chem. Ref. Data, vol. 9, No. 3, 1980, 98 pages.

Myrick, "Multivariate optical elements simplify spectroscopy," Laser Focus World, Mar. 1, 2002, access date Feb. 28, 2013, 3 pages http://www.laserfocusworld.com/articles/print/volume-38/issue-3/features/spectroscopy/multivariate-optical-elements-simplify-spectroscopy.html.

Myrick et al., "A single-element all-optical approach to chemometric prediction," Vibrational Spectroscopy 28, 2002, 9 pages.

Myrick et al., "Spectral tolerance determination for multivariate optical element design," Fresenius J Anal Chem, 369, 2001, 5 pages.

Myrick et al., "Application of multivariate optical computing to simple near-infrared point measurements," SPIE vol. 4574, Department of Chemistry and biochemistry, University of South Carolina, 2002, 8 pages.

Rabady et al., "High-resolution photometric optical monitoring for thin-film deposition," Applied Optics, Optical Society of America, vol. 43, No. 1, Jan. 1, 2004, 6 pages.

Priore et al., "Novel Imaging Systems: Multivariate Optical Computing in the UV-VIS," Department of Chemistry and Biochemistry, University of South Carolina, 2003, 5 pages.

Grader et al., "Fourier transform infrared spectroscopy of a single aerosol particle," J. Chem. Phys. 86 (11), Jun. 1, 1987, 7 pages.

Soyemi et al., "Novel Filter Design Algorithm for Multivariate Optical Computing," Advanced Environmental and Chemical Sensing Technology, SPIE vol. 4205, 2001, 12 pages.

Telemark, "Model 820 In-Situ Spectroscopic Optical Monitor," Dec. 2010, 4 pages.

Bossard et al., "The Design and fabrication of planar multiband metallodielectric frequency selective surfaces for infrared applications", IEEE Trans. On Antennas and Propagation, v. 50, No. 4, Apr. 2006, 12 pages.

Woollam et al., "Overview of Variable Angle Spectroscopic Ellipsometer (VASE), Part 1: Basic Theory and Typical Applications," Society of Photo-Optical Instrumentation Engineers, Critical Reviews of Optical Science Technology CR72, 1999, 28 pages.

Zoeller et al., "Substantial progress in optical monitoring by intermittent measurement technique," SPIE, Published in the processing of the OSD, Jena 2005, vol. 5963-13, 9 pages.

Haibach et al., "On-line Reoptimization of Filter Designs for Multivariate Optical Elements," vol. 42, No. 10, Apr. 1, 2003.

Communication Pursuant to Article 94(3) issued in European Application No. 13885459.1, dated Jun. 14, 2016.

* cited by examiner

ADJUSTING FABRICATION OF INTEGRATED COMPUTATIONAL ELEMENTS

CLAIM OF PRIORITY

This application is a U.S. National Stage of International Application No. PCT/US2013/077683, filed Dec. 24, 2013.

BACKGROUND

The subject matter of this disclosure is generally related to fabrication of an integrated computational element (ICE) used in optical analysis tools for analyzing a substance of interest, for example, crude petroleum, gas, water, or other wellbore fluids. For instance, the disclosed adjustments to ICE fabrication include changing a specified total number of layers of the ICE during the ICE fabrication to a new total number of layers to recover at least some of performance degradation of the ICE caused by errors associated with the ICE fabrication.

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

Integrated computational elements (ICEs) enable the measurement of various chemical or physical characteristics through the use of regression techniques. An ICE selectively weights, when operated as part of optical analysis tools, light modified by a sample in at least a portion of a wavelength range such that the weightings are related to one or more characteristics of the sample. An ICE can be an optical substrate with multiple stacked dielectric layers (e.g., from about 2 to about 50 layers), each having a different complex refractive index from its adjacent layers. The specific number of layers, N, the optical properties (e.g. real and imaginary components of complex indices of refraction) of the layers, the optical properties of the substrate, and the physical thickness of each of the layers that compose the ICE are selected so that the light processed by the ICE is related to one or more characteristics of the sample. Because ICEs extract information from the light modified by a sample passively, they can be incorporated in low cost and rugged optical analysis tools. Hence, ICE-based downhole optical analysis tools can provide a relatively low cost, rugged and accurate system for monitoring quality of wellbore fluids, for instance.

Errors in fabrication of some constituent layers of an ICE design can degrade the ICE's target performance. In most cases, deviations of <0.1%, and even 0.01% or 0.0001%, from point by point design values of the optical characteristics (e.g., complex refractive indices), and/or physical characteristics (e.g., thicknesses) of the formed layers of the ICE can reduce the ICE's performance, in some cases to such an extent, that the ICE becomes operationally useless. Those familiar or currently practicing in the art will readily appreciate that the ultra-high accuracies required by ICE designs challenge the state of the art in techniques for adjusting thin film stack fabrication.

Conventionally, prior to or while forming of each of the total number of layers of the ICE, target thicknesses of one or more layers that remain to be formed are updated based on complex refractive indices and thicknesses of the formed layers. In this manner, degradation in the ICE performance relative to the target performance, caused by inaccuracies in the complex refractive indices and thicknesses of the formed layers, can be minimized while forming the remaining ones of the total number of layers. An additional conventional modification of the ICE fabrication relates to skipping the forming of a layer when the layer's updated target thickness is smaller than a minimum thickness allowed by capability of the ICE fabrication.

DESCRIPTION OF DRAWINGS

Like reference symbols in the various drawings indicate like elements.

DETAILED DESCRIPTION

Technologies are described for in-situ adjusting ICE fabrication by changing a specified total number of layers of an ICE to a new total number of layers when it is predicted, during the ICE fabrication, that performance degradation of the ICE fabricated with the specified total number of layers exceeds a maximum allowed performance degradation. In this manner, the performance degradation of the ICE fabricated with the new total number of layers can be maintained under the maximum allowed performance degradation. The maximum allowed performance degradation corresponds to a minimum acceptable accuracy with which the ICE should predict the known values of the characteristic corresponding to the validation spectra of the sample. A number of layers added to or subtracted from the specified total number of layers is obtained based on (i) the relative difference between the predicted performance degradation and the maximum allowed performance degradation, and/or (ii) fabrication process/equipment capability.

The disclosed technologies can be used to implement ICE fabrication that can be more accurate than conventional ICE fabrication. For instance, a potential advantage of the disclosed technologies is that by allowing additional layers to be formed, an optimization for minimizing the performance degradation of the ICE formed with the new total number of layers gains additional degrees of freedom. Here, a global (or local) extremum that satisfies the maximum allowed performance degradation is potentially more feasible to find, and if so can be found faster in a parameter space associated with the new total number of layers than in the parameter space—with fewer available parameters—associated with the specified total number of layers. The latter parameter space is used for the optimization process in the conventional ICE fabrication.

The disclosed technologies also can be used to advantageously implement ICE fabrication that can be less time consuming then conventional ICE fabrication. For instance, by allowing to subtract layers from the specified total number of layers, during the ICE fabrication when the predicted performance degradation of the ICE formed with fewer than the specified total number of layers is at most equal to the maximum allowed performance degradation, the disclosed ICE fabrication can be sped up relative to the conventional ICE fabrication by skipping deposition of the subtracted layers.

Prior to describing example implementations of the disclosed technologies for ICE fabrication, the following technologies are described below: in Section (1)—optical analysis tools based on ICE along with examples of their use in oil/gas exploration, and in Section (2)—techniques for designing an ICE.

(1) ICE-Based Analysis of Wellbore Fluids

Figure 1A:
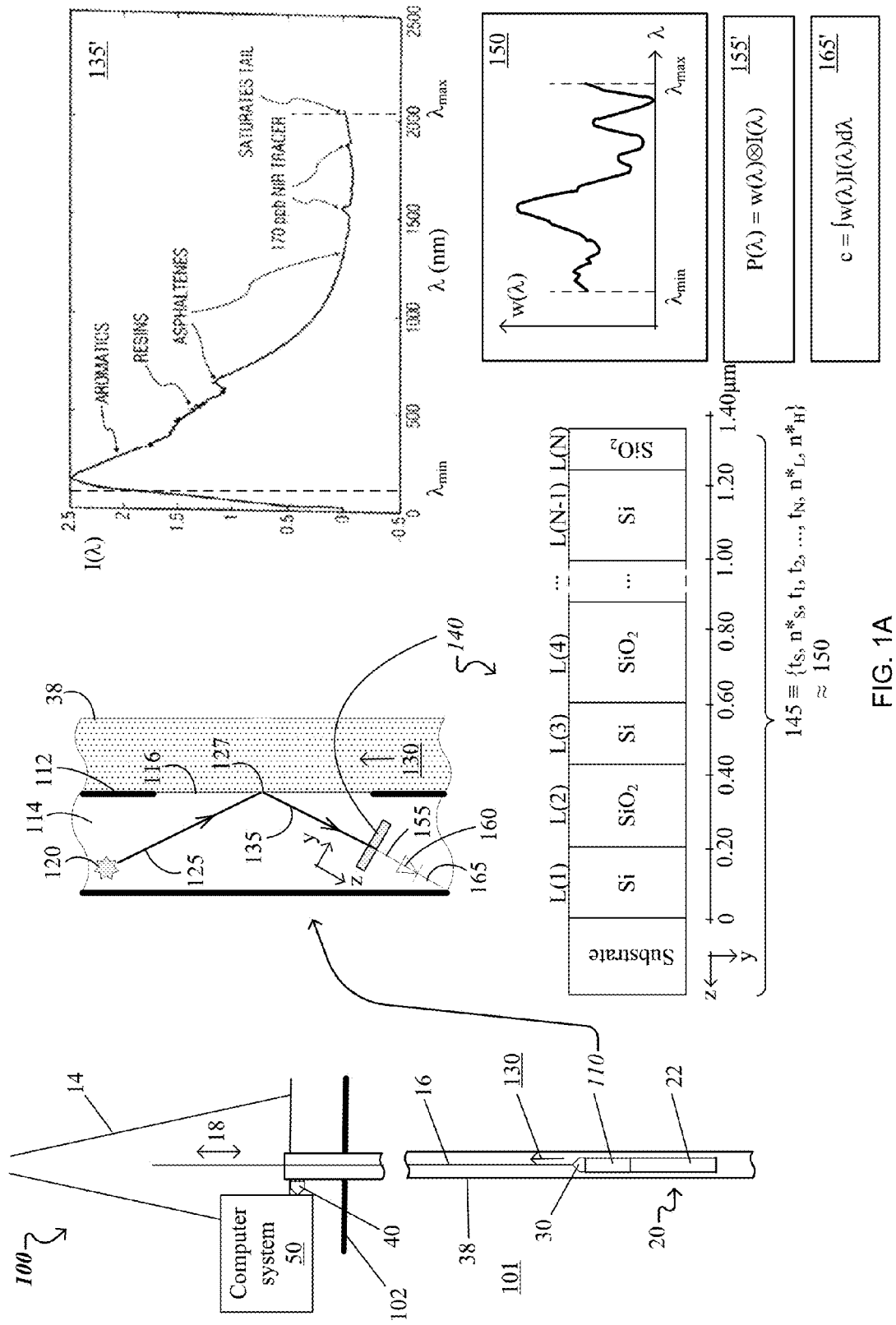
FIGS. 1A-1C show multiple configurations of an example of a system for analyzing wellbore fluids that uses a well logging tool including an ICE.
Figure 1C:
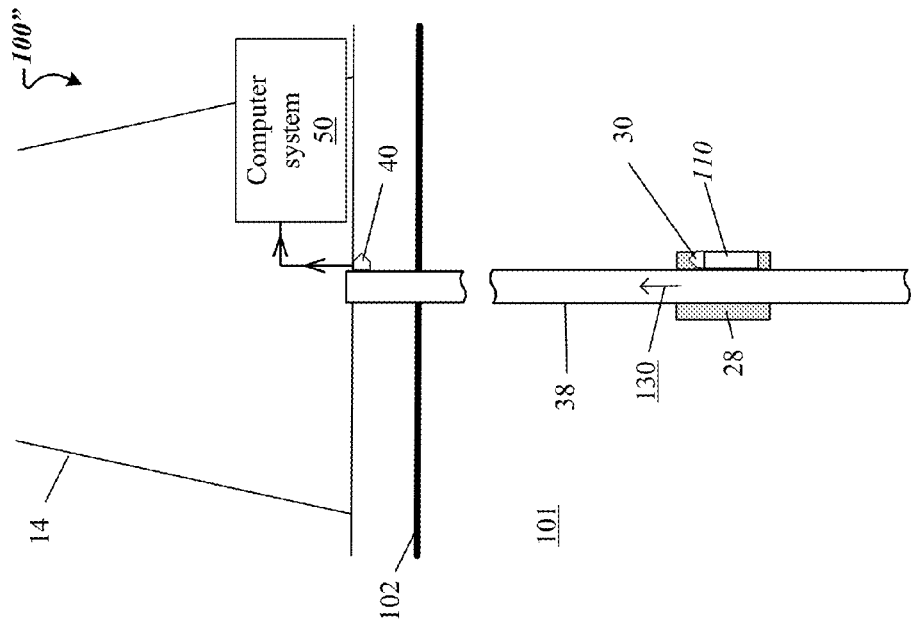
Figure 1B:
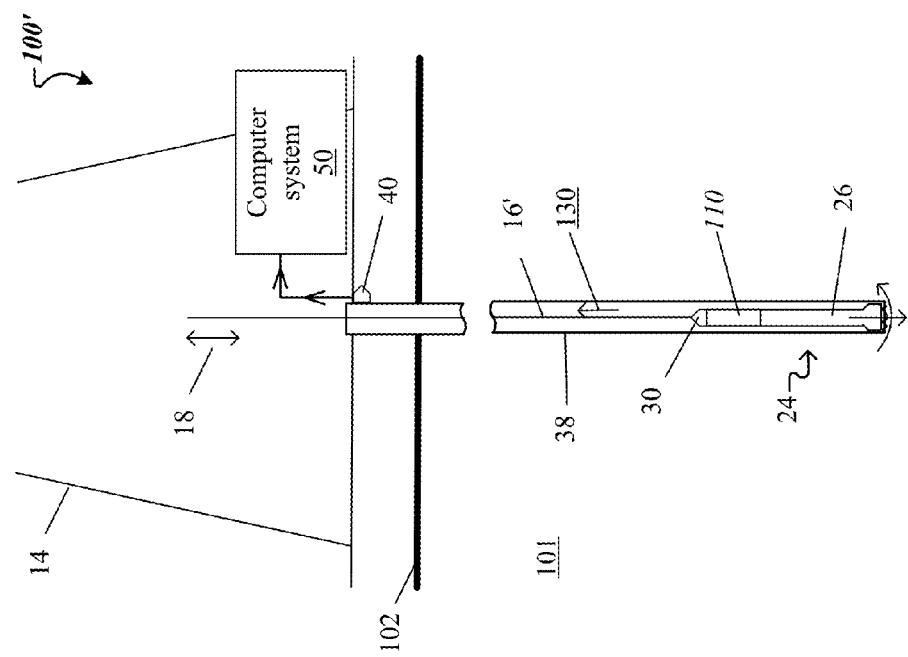

FIGS. 1A-1C show multiple configurations 100, 100', 100" of an example of a system for analyzing wellbore fluids 130, such that analyses are generated from measurements taken with a well logging tool 110 configured as an ICE-based optical analysis tool. The disclosed system also is referred to as a well logging system.

Each of the configurations 100, 100', 100" of the well logging system illustrated in FIGS. 1A-1C includes a rig 14 above the ground surface 102 and a wellbore 38 below the ground surface. The wellbore 38 extends from the ground surface into the earth 101 and generally passes through multiple geologic formations. In general, the wellbore 38 can contain wellbore fluids 130. The wellbore fluids 130 can be crude petroleum, mud, water or other substances and combinations thereof. Moreover, the wellbore fluids 130 may be at rest, or may flow toward the ground surface 102, for instance. Additionally, surface applications of the well logging tool 110 may include water monitoring and gas and crude transportation and processing.

FIG. 1A shows a configuration 100 of the well logging system which includes a tool string 20 attached to a cable 16 that can be lowered or raised in the wellbore 38 by draw works 18. The tool string 20 includes measurement and/or logging tools to generate and log information about the wellbore fluids 130 in the wellbore 38. In the configuration 100 of the well logging system, this information can be generated as a function of a distance (e.g., a depth) with respect to the ground surface 102. In the example illustrated in FIG. 1A, the tool string 20 includes the well logging tool 110, one or more additional well logging tool(s) 22, and a telemetry transmitter 30. Each of the well logging tools 110 and 22 measures one or more characteristics of the wellbore fluids 130. In some implementations, the well logging tool 110 determines values of the one or more characteristics in real time and reports those values instantaneously as they occur in the flowing stream of wellbore fluids 130, sequentially to or simultaneously with other measurement/logging tools 22 of the tool string 20.

FIG. 1B shows another configuration 100' of the well logging system which includes a drilling tool 24 attached to a drill string 16'. The drilling tool 24 includes a drill bit 26, the ICE-based well logging tool 110 configured as a measurement while drilling (MWD) and/or logging while drilling (LWD) tool, and the telemetry transmitter 30. Drilling mud is provided through the drill string 16' to be injected into the borehole 38 through ports of the drill bit 26. The injected drilling mud flows up the borehole 38 to be returned above the ground level 102, where the returned drilling mud can be resupplied to the drill string 16' (not shown in FIG. 1B). In this case, the MWD/LWD-configured well logging tool 110 generates and logs information about the wellbore fluids 130 (e.g., drilling mud in this case) adjacent the working drill bit 26.

FIG. 1C shows yet another configuration 100" of the well logging system which includes a permanent installation adjacent to the borehole 38. In some implementations, the permanent installation is a set of casing collars that reinforce the borehole 38. In this case, a casing collar 28 from among the set of casing collars supports the well logging tool 110 and the telemetry transmitter 30. In this manner, the well logging tool 110 determines and logs characteristics of the wellbore fluids 130 adjacent the underground location of the casing collar 28.

In each of the above configurations 100, 100' and 100" of the well logging system, the values of the one or more characteristics measured by the well logging tool 110 are provided (e.g., as a detector signal 165) to the telemetry transmitter 30. The latter communicates the measured values to a telemetry receiver 40 located above the ground surface 102. The telemetry transmitter 30 and the telemetry receiver 40 can communicate through a wired or wireless telemetry channel. In some implementations of the system configurations 100, 100' illustrated in FIGS. 1A and 1B, e.g., in slickline or coiled tubing applications, measurement data generated by the well logging tool 110 can be written locally to memory of the well logging tool 110.

The measured values of the one or more characteristics of the wellbore fluids 130 received by the telemetry receiver 40 can be logged and analyzed by a computer system 50 associated with the rig 14. In this manner, the measurement values provided by the well logging tool 110 can be used to generate physical and chemical information about the wellbore fluids 130 in the wellbore 38.

Referring again to FIG. 1A, the well logging tool 110 includes a light source 120, an ICE 140 and an optical transducer 160. The well logging tool 110 has a frame 112 such that these components are arranged in an enclosure 114 thereof. A cross-section of the well logging tool 110 in a plane perpendicular to the page can vary, depending on the space available. For example, the well logging tool's cross-section can be circular or rectangular, for instance. The well logging tool 110 directs light to the sample 130 through an optical interface 116, e.g., a window in the frame 112. The well logging tool 110 is configured to probe the sample 130 (e.g., the wellbore fluids stationary or flowing) in the wellbore 38 through the optical interface 116 and to determine an amount (e.g., a value) of a given characteristic (also referred to as a characteristic to be measured) of the probed sample 130. The characteristic to be measured can be any one of multiple characteristics of the sample 130 including concentration of a given substance in the sample, a gas-oil-ratio (GOR), pH value, density, viscosity, etc.

The light source 120 outputs light with a source spectrum over a particular wavelength range, from a minimum wavelength $\lambda_{min}$ to a maximum wavelength $\lambda_{max}$. In some implementations, the source spectrum can have non-zero intensity over the entire or most of the wavelength range $\lambda_{max}$-$\lambda_{min}$. In some implementations, the source spectrum extends through UV-vis (0.2-0.8 µm) and near-IR (0.8-2.5 µm) spectral ranges. Alternatively, or additionally, the source spectrum extends through near-IR and mid-IR (2.5-25 μm) spectral ranges. In some implementations, the source spectrum extends through near-IR, mid-IR and far-IR (25-100 μm) spectral ranges. In some implementations, the light source 120 is tunable and is configured in combination with time resolved signal detection and processing.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The light modified by the sample has a modified spectrum $I(\lambda)$ 135' over the particular wavelength range. In the reflective configuration of the well logging tool 110 illustrated in FIG. 1A (i.e., where the light to be analyzed reflects at the sample/window interface), the modified spectrum $I(\lambda)$ 135' is a reflection spectrum associated with the sample 130. In a transmission configuration of the well logging tool 110 (not shown in FIG. 1A), the probe beam is transmitted through the sample as modified light, such that the modified spectrum $I(\lambda)$ 135' is a transmission spectrum associated with the sample.

In general, the modified spectrum $I(\lambda)$ 135' encodes information about multiple characteristics associated with the sample 130, and more specifically the encoded information relates to current values of the multiple characteristics. In the example illustrated in FIG. 1A, the modified spectrum 135' contains information about one or more characteristics of the wellbore fluids 130.

With continued reference to FIG. 1A, and the Cartesian coordinate system provided therein for reference, the ICE 140 is arranged to receive a beam 135 of the sample modified light, and is configured to process it and to output a beam 155 of processed light. The beam 135 of sample modified light is incident on a first surface of the ICE 140 along the z-axis, and the beam 155 of processed light is output along the z-axis after transmission through the ICE 140. Alternatively or additionally, the beam 155 (or an additional reflected beam) of processed light can be output after reflection off the first surface of the ICE 140. The ICE 140 is configured to process the sample modified light by weighting it in accordance with an optical spectrum $w(\lambda)$ 150 associated with a characteristic to be measured.

The optical spectrum $w(\lambda)$ 150 is determined offline by applying conventional processes to a set of calibration spectra $I(\lambda)$ of the sample which correspond to respective known values of the characteristic to be measured. As illustrated by optical spectrum $w(\lambda)$ 150, optical spectrums generally may include multiple local maxima (peaks) and minima (valleys) between $\lambda_{min}$ and $\lambda_{max}$. The peaks and valleys may have the same or different amplitudes. For instance, an optical spectrum $w(\lambda)$ can be determined through regression analysis of $N_c$ calibration spectra $I_j(\lambda)$ of a sample, where j=1, . . . , $N_c$, such that each of the calibration spectra $I_j(\lambda)$ corresponds to an associated known value of a given characteristic for the sample. A typical number $N_c$ of calibration spectra $I_j(\lambda)$ used to determine the optical spectrum $w(\lambda)$ 150 through such regression analysis can be $N_c$=10, 40 or 100, for instance. The regression analysis outputs, within the $N_c$ calibration spectra $I_j(\lambda)$, a spectral pattern that is unique to the given characteristic. The spectral pattern output by the regression analysis corresponds to the optical spectrum $w(\lambda)$ 150. In this manner, when a value of the given characteristic for the sample is unknown, a modified spectrum $I_u(\lambda)$ of the sample is acquired by interacting the probe beam 125 with the sample 130, then the modified spectrum $I_u(L)$ is weighted with the ICE 140 to determine a magnitude of the spectral pattern corresponding to the optical spectrum $w(\lambda)$ 150 within the modified spectrum $I_u(\lambda)$. The determined magnitude is proportional to the unknown value of the given characteristic for the sample.

For example, the sample can be a mixture (e.g., the wellbore fluid 130) containing substances X, Y and Z, and the characteristic to be measured for the mixture is concentration $c_X$ of substance X in the mixture. In this case, $N_c$ calibration spectra $I_j(\lambda)$ were acquired for $N_c$ samples of the mixture having respectively known concentration values for each of the substances contained in the $N_c$ samples. By applying regression analysis to the $N_c$ calibration spectra $I_j(\lambda)$, a first spectral pattern that is unique to the concentration $c_X$ of the X substance can be detected (recognized), such that the first spectral pattern corresponds to a first optical spectrum $w_{cX}(\lambda)$ associated with a first ICE, for example. Similarly, second and third spectral patterns that are respectively unique to concentrations $c_Y$ and $c_Z$ of the Y and Z substances can also be detected, such that the second and third spectral patterns respectively correspond to second and third optical spectra $w_{cY}(\lambda)$ and $w_{cZ}(\lambda)$ respectively associated with second and third ICEs. In this manner, when a new sample of the mixture (e.g., the wellbore fluid 130) has an unknown concentration $c_X$ of the X substance, for instance, a modified spectrum $I_u(\lambda)$ of the new sample can be acquired by interacting the probe beam with the mixture, then the modified spectrum $Iu(\lambda)$ is weighted with the first ICE to determine a magnitude of the first spectral pattern within the modified spectrum $I_u(\lambda)$. The determined magnitude is proportional to the unknown value of the concentration $c_X$ of the X substance for the new sample.

Referring again to FIG. 1A, the ICE 140 includes N layers of materials stacked on a substrate, such that complex refractive indices of adjacent layers are different from each other. The total number of stacked layers can be between 6 and 50, for instance. The substrate material can be BK7, diamond, Ge, ZnSe (or other transparent dielectric material), and can have a thickness in the range of 0.02-2 mm, for instance, to insure structural integrity of the ICE 140.

Throughout this specification, a complex index of refraction (or complex refractive index) $n^*$ of a material has a complex value, $Re(n^*)+iIm(n^*)$. $Re(n^*)$ represents a real component of the complex index of refraction responsible for refractive properties of the material, and $Im(n^*)$ represents an imaginary component of the complex index of refraction (also known as extinction coefficient κ) responsible for absorptive properties of the material. In this specification, when it is said that a material has a high complex index of refraction $n^*_H$ and another material has a low complex index of refraction $n^*_L$, the real component $Re(n^*_H)$ of the high complex index of refraction $n^*_H$ is larger than the real component $Re(n^*_L)$ of the low complex index of refraction $n^*_L$, $Re(n^*_H) > Re(n^*_H)$. Materials of adjacent layers of the ICE are selected to have a high complex index of refraction $n^*_H$ (e.g., Si), and a low complex index of refraction $n^*_L$ (e.g., $SiO_2$). Here, $Re(n^*_{Si}) \approx 2.4 > Re(n^*_{SiO2}) \approx 1.5$. For other material pairings, however, the difference between the high complex refractive index $n^*_H$ and low complex refractive index $n^*_L$ may be much smaller, e.g., $Re(n^*_H) \approx 1.6 > Re(n^*_L) \approx 1.5$. The use of two materials for fabricating the N layers is chosen for illustrative purposes only. For example, a plurality of materials having different complex indices of refraction, respectively, can be used. Here, the materials used to construct the ICE are chosen to achieve a desired optical spectrum $w(\lambda)$ 150.

A set of design parameters 145—which includes the total number of stacked layers N, the complex refractive indices $n^*_H$, $n^*_L$ of adjacent stacked layers, and the thicknesses of the N stacked layers t(1), t(2), . . . , t(N−1), t(N)—of the ICE 140 can be chosen (as described below in connection with FIG. 2) to be spectrally equivalent to the optical spectrum w(λ) 150 associated with the characteristic to be measured. As such, an ICE design includes a set 145 of thicknesses {t(i), i=1, . . . , N} of the N layers stacked on the substrate that correspond to the optical spectrum w(λ) 150.

In view of the above, the beam 155 of processed light output by the ICE 140 has a processed spectrum $P(\lambda)=w(\lambda) \otimes I(\lambda)$ 155' over the wavelength range $\lambda_{max}$-$\lambda_{min}$, such that the processed spectrum 155' represents the modified spectrum I(80) 135' weighted by the optical spectrum w(λ) 150 associated with the characteristic to be measured.

The beam 155 of processed light is directed from the ICE 140 to the optical transducer 160, which detects the processed light and outputs an optical transducer signal 165. A value (e.g., a voltage) of the optical transducer signal 165 is a result of an integration of the processed spectrum 155' over the particular wavelength range and is proportional to the unknown value "c" 165' of the characteristic to be measured for the sample 130.

In some implementations, the well logging tool 110 can include a second ICE (not shown in FIG. 1A) associated with a second ICE design that includes a second set of thicknesses {t'(i), i=1, . . . , N'} of a second total number N' of layers, each having a different complex refractive index from its adjacent layers, the complex refractive indices and the thicknesses of the N' layers corresponding to a second optical spectrum w'(λ). Here, the second optical spectrum w'(λ) is associated with a second characteristic of the sample 130, and a second processed spectrum represents the modified spectrum I(λ) 135' weighted by the second optical spectrum w'(λ), such that a second value of a second detector signal is proportional to a value of the second characteristic for the sample 130.

In some implementations, the determined value 165' of the characteristic to be measured can be logged along with a measurement time, geo-location, and other metadata, for instance. In some implementations, the detector signal 165, which is proportional to a characteristic to be measured by the well logging tool 110, can be used as a feedback signal to adjust the characteristic of the sample, to modify the sample or environmental conditions associated with the sample, as desired.

Characteristics of the wellbore fluids 130 that can be related to the modified spectrum 135' through the optical spectra associated with the ICE 140 and other ICEs (not shown in FIG. 1A) are concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

(2) Aspects of ICE Design

Aspects of a process for designing an ICE associated with a characteristic to be measured (e.g., one of the characteristics enumerated above) are described below. Here, an input of the ICE design process is a theoretical optical spectrum $w_{th}(\lambda)$ associated with the characteristic. An output of the ICE design process is an ICE design that includes specification of (1) a substrate and a number N of layers to be formed on the substrate, each layer having a different complex refractive index from its adjacent layers; and (2) complex refractive indices and thicknesses of the substrate and layers that correspond to a target optical spectrum $w_t(\lambda)$. The target optical spectrum $w_t(\lambda)$ is different from the theoretical optical spectrum $w_{th}(\lambda)$ associated with the characteristic, such that the difference between the target and theoretical optical spectra cause degradation of a target performance relative to a theoretical performance of the ICE within a target error tolerance. The target performance represents a finite accuracy with which an ICE having the target optical spectrum $w_t(\lambda)$ is expected to predict known values of the characteristic corresponding to a set of validation spectra of a sample with a finite (non-zero) error. Here, the predicted values of the characteristic are obtained through integration of the validation spectra of the sample respectively weighted by the ICE with the target optical spectrum $w_t(\lambda)$. The theoretical performance represents the maximum accuracy with which the ICE—if it had the theoretical optical spectrum $w_{th}(\lambda)$—would predict the known values of the characteristic corresponding to the set of validation spectra of the sample. Here, the theoretically predicted values of the characteristic would be obtained through integration of the validation spectra of the sample respectively weighted by the ICE, should the ICE have the theoretical optical spectrum $w_{th}(\lambda)$.

Figure 2:
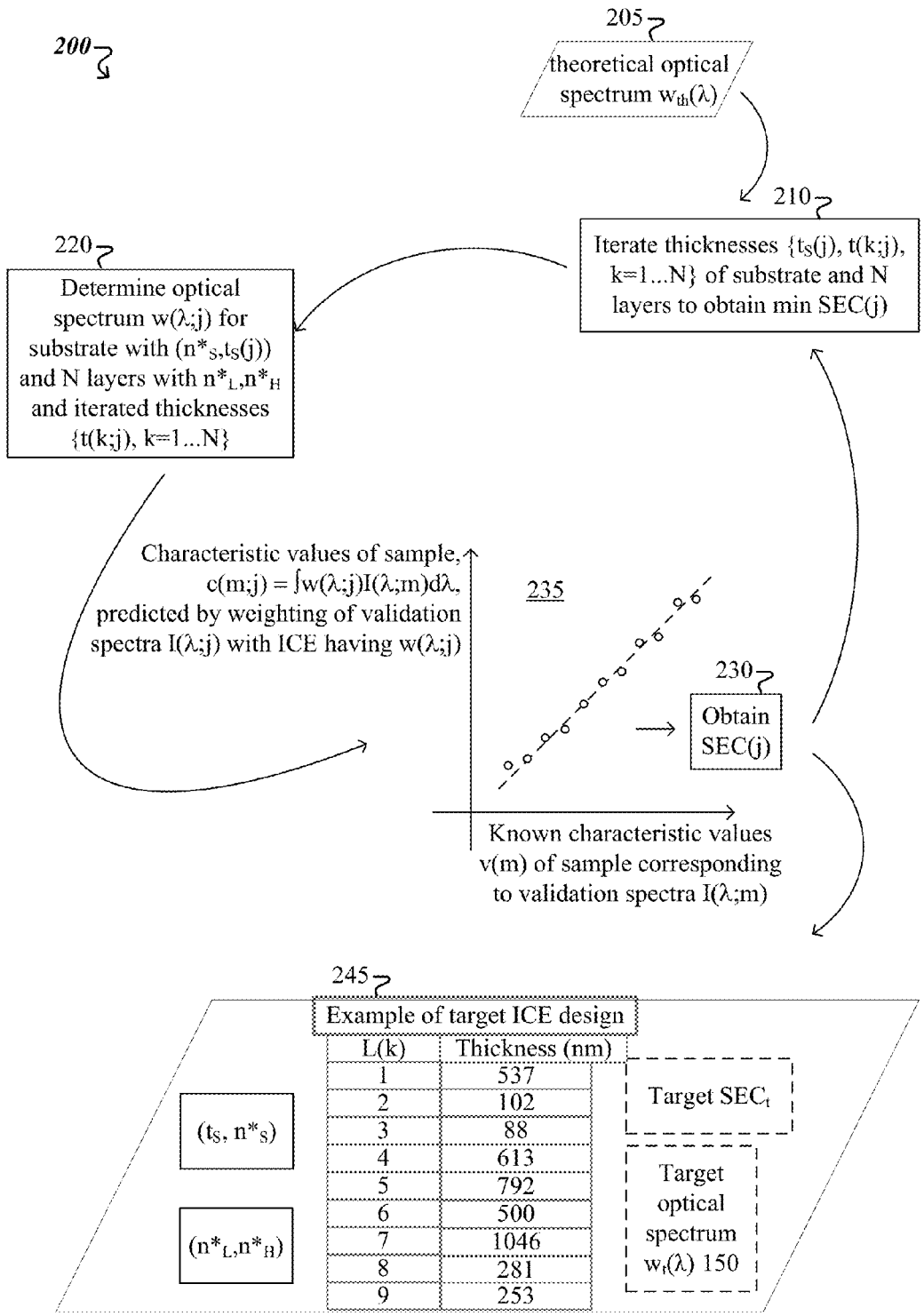
FIG. 2 is a flowchart showing an example of a process for designing an ICE.

FIG. 2 is a flow chart of an example of a process 200 for generating an ICE design. One of the inputs to the process 200 is a theoretical optical spectrum $w_{th}(\lambda)$ 205. For instance, to design an ICE for measuring concentration of a substance X in a mixture, a theoretical optical spectrum $w_{th}(\lambda)$, associated with the concentration of the substance X in the mixture, is accessed, e.g., in a data repository. As described above in this specification, the accessed theoretical optical spectrum $w_t(\lambda)$ corresponds to a spectral pattern detected offline, using a number $N_c$ of calibration spectra of the mixture, each of the $N_c$ calibration spectra corresponding to a known concentration of the substance X in the mixture. An additional input to the process 200 is a specification of materials for a substrate and ICE layers. Materials having different complex refractive indices, respectively, are specified such that adjacent ICE layers are formed from materials with different complex refractive indices. For example, a first material (e.g., Si) having a high complex refractive index $n^*_H$ and a second material (e.g., $SiO_x$) having a low complex refractive index $n^*_L$ are specified to alternately form the ICE layers. As another example, a layer can be made from high index material (e.g., Si), followed by a layer made from low index material (e.g., $SiO_x$), followed by a layer made from a different high index material (e.g., Ge), followed by a layer made from a different low index material ($MgF_2$), etc. The iterative design process 200 is performed in the following manner.

At 210 during the $j^{th}$ iteration of the design process 200, thicknesses {$t_s(j)$, t(1;j), t(2;j), . . . , t(N−1;j), t(N;j)} of the substrate and a number N of layers of the ICE are iterated.

At 220, a $j^{th}$ optical spectrum w(λ;j) of the ICE is determined corresponding to complex refractive indices and previously iterated thicknesses {$t_s(j)$, t(1;j), t(2;j), . . . , t(N−1;j), t(N;j)} of the substrate and the N layers, each having a different complex refractive index from its adjacent layers. The iterated thicknesses of the substrate and the N layers are used to determine the corresponding $j^{th}$ optical spectrum $w(\lambda;j)$ of the ICE in accordance with conventional techniques for determining spectra of thin film interference filters.

At 230, performance of the ICE, which has the $j^{th}$ optical spectrum $w(\lambda;j)$ determined at 220, is obtained. To do so, a set of validation spectra of a sample is accessed, e.g., in a data repository. Respective values of a characteristic of the sample are known for the validation spectra. For instance, each of $N_v$ validation spectra $I(\lambda;m)$ corresponds to a value $v(m)$ of the characteristic of the sample, where $m=1, \ldots, N_v$. In the example illustrated in FIG. 2, $N_v=11$ validation spectra, respectively corresponding to 11 known values of the characteristic to be measured for the sample, are being used.

Graph 235 shows (in open circles) values $c(m;j)$ of the characteristic of the sample predicted by integration of the validation spectra $I(\lambda;m)$ weighted with the ICE, which has the $j^{th}$ optical spectrum $w(\lambda;j)$, plotted against the known values $v(m)$ of the characteristic of the sample corresponding to the validation spectra $I(\lambda;m)$. The predicted values $c(m;1)$ of the characteristic are found by substituting, in formula 165' of FIG. 1A, (1) the spectrum $I(\lambda)$ 135' of sample modified light with the respective validation spectra $I(\lambda;m)$ and (2) the target spectrum $w_t(\lambda)$ 150 with the $j^{th}$ optical spectrum $w(\lambda;j)$. In this example, performance of the ICE, which has the $j^{th}$ optical spectrum $w(\lambda;j)$, is quantified in terms of a weighted measure of distances from each of the open circles in graph 325 to the dashed-line bisector between the x and y axes. This weighted measure is referred to as the standard calibration error (SEC) of the ICE. For instance, an ICE having the theoretical spectrum $w_{th}(\lambda)$ has a theoretical $SEC_{th}$ that represents a lower bound for the $SEC(j)$ of the ICE having the $j^{th}$ spectrum $w(\lambda;j)$ determined at 220 during the $j^{th}$ iteration of the design process 200: $SEC(j) > SEC_{th}$.

In this specification, the SEC is chosen as a metric for evaluating ICE performance for the sake of simplicity. Note that there are other figures of merit that may be used to evaluate performance of ICE, as is known in the art. For example, sensitivity—which is defined as the slope of characteristic change as a function of signal strength—can also be used to evaluate ICE performance As another example, standard error of prediction (SEP)—which is defined in a similar manner to the SEC except it uses a different set of validation spectra—can be used to evaluate ICE performance. Any of the figure(s) of merit known in the art is/are evaluated in the same general way by comparing theoretical performance with that actually achieved. Which figure(s) of merit or combinations are used to evaluate ICE performance is determined by the specific ICE design.

The iterative design process 200 continues by iterating, at 210, the thicknesses of the substrate and the N layers. The iterating is performed such that a $(j+1)^{th}$ optical spectrum $w(\lambda;j+1)$—determined at 220 from the newly iterated thicknesses—causes, at 230, improvement in performance of the ICE, to obtain $SEC(j+1) < SEC(j)$. In some implementations, the iterative design process 200 is stopped when the ICE's performance reaches a local maximum, or equivalently, the SEC of the ICE reaches a local minimum. For example, the iterative process 200 can be stopped at the $(j+1)^{th}$ iteration when the current $SEC(j+1)$ is larger than the last $SEC(j)$, $SEC(j+1) > SEC(j)$. In some implementations, the iterative design process 200 is stopped when, for a given number of iterations, the ICE's performance exceeds a specified threshold performance for a given number of iterations. For example, the iterative design process 200 can be stopped at the $j^{th}$ iteration when three consecutive SEC values decrease monotonously and are less than a specified threshold value: $SEC_0 > SEC(j-2) > SEC(j-1) > SEC(j)$.

In either of these cases, an output of the iterative process 200 represents a target ICE design 245 to be used for fabricating an ICE 140, like the one described in FIG. 1A, for instance. The ICE design 245 includes specification of (1) a substrate and N layers, each having a different complex refractive index from its adjacent layers, and (2) complex refractive indices $n^*_S$, $n^*_H$, $n^*_L$ and thicknesses $\{t_s(j), t(1;j), t(2;j), \ldots, t(N-1;j), t(N;j)\}$ of the substrate and N layers corresponding to the $j^{th}$ iteration of the process 200. Additional components of the ICE design are the optical spectrum $w(\lambda;j)$ and the $SEC(j)$—both determined during the $j^{th}$ iteration based on the thicknesses $\{t_s(j), t(1;j), t(2;j), \ldots, t(N-1;j), t(N;j)\}$. As the ICE design 245 is used as input for fabrication processes described herein, the iteration index j—at which the iterative process 200 terminates—is dropped from the notations used for the components of the ICE design.

In this manner, the thicknesses of the substrate and the N layers associated with the ICE design 245 are denoted $\{t_s, t(1), t(2), t(N-1), t(N)\}$ and are referred to as the target thicknesses. The optical spectrum associated with the ICE design 245 and corresponding to the target thicknesses is referred to as the target optical spectrum $w_t(\lambda)$ 150. The SEC associated with the ICE design 245—obtained in accordance with the target optical spectrum $w_t(\lambda)$ 150 corresponding to the target thicknesses—is referred to as the target $SEC_t$. In the example illustrated in FIG. 2, the ICE design 245 has a total of N=9 alternating Si and $SiO_2$ layers, with complex refractive indices $n_{Si}$, $n_{SiO2}$, respectively. The layers' thicknesses (in nm) are shown in the table. An ICE fabricated based on the example of ICE design 245 illustrated in FIG. 2 is used to predict value(s) of concentration of substance X in wellbore fluids 130.

(3) Technologies for Adjusting Fabrication of ICE

As described above in connection with FIG. 2, an ICE design specifies a number of material layers), each having a different complex refractive index from its adjacent layers. An ICE fabricated in accordance with the ICE design has (i) a target optical spectrum $w_t(\lambda)$ and (ii) a target performance $SEC_t$, both of which corresponding to the complex refractive indices and target thicknesses of a substrate and a total number of layers specified by the ICE design. Performance of the ICE fabricated in accordance with the ICE design can be very sensitive to actual values of the complex refractive indices and thicknesses obtained during deposition. For a wide variety of reasons, the actual values of the complex refractive indices of materials to be deposited and/or the rate(s) of the deposition may drift within a fabrication batch or batch-to-batch, or may be affected indirectly by errors caused by measurement systems used to control the foregoing fabrication parameters. For example, materials used for deposition (Si, $SiO_2$) may be differently contaminated, or react differently due to different chamber conditions (e.g., pressure or temperature). For some layers of the ICE design 245, a small error, e.g., 0.1% or 0.001%, in the thickness of a deposited layer can result in a reduction in the performance of an ICE associated with the ICE design 245 below an acceptable threshold.

Some conventional processes for fabricating optical thin films are generally implemented such that each layer of the specified total number of layers is deposited continuously until that the desired thickness is achieved. For example, $3^{rd}$ layer L(3) of the ICE design 245, which is specified to be 88 nm thick Si layer, is deposited in a single deposition sequence. In some such cases (e.g., described below in connection with FIG. 5), an error or miscalculation in deposition rate, e.g., 1%, can lead to depositing the $3^{rd}$ layer L(3) with a thickness that is 32 nm (36%) too thick. In general, if this error and other such or different errors (sometimes as small as e.g., 0.1% or 0.001% in the thickness of a deposited layer) are introduced during fabrication of other remaining layers of specified by the ICE design, there may be a reduction in the performance of the ICE associated with an ICE design below an acceptable threshold.

Effects of fabrication errors on the performance of fabricated ICEs are minimized by monitoring the ICE fabrication. Also, the ICE design can be modified during ICE fabrication to regain at least some of the degradation of ICE performance induced by the fabrication errors. Modifications of an ICE design conventionally include updating target thicknesses for layers remaining to be form from the specified total number of layers. In this case, updating the ICE design during fabrication in a conventional manner results in an updated ICE design that has the same total number of layers as originally specified. Another conventional modification of the ICE design is removing of a layer of the specified total number of layers if its updated target thickness is too thin, for example thinner than deposition capability (e.g., <$t_{min}$=10 nm, in some cases). Here, updating the ICE design during fabrication results in an updated ICE design that has fewer layers than originally specified.

The technologies described herein can be used to regain at least some of degradation of ICE performance induced by fabrication errors by allowing additional layers to be added to or some layers to be removed from an ICE design, during ICE fabrication. In some implementations, additional layers are deposited at the top of a stack with the original total number of layers as terminating layers, for example. As another example, the additional layers are inserted in the middle of the stack. In other implementations, one or more layers can be removed from the top of the stack with the original total number of layers, for example. As another example, two or more layers can be removed from the middle of the stack.

Details of one or more of the foregoing embodiments are described below.

(3.1) System for ICE Fabrication With In-Situ Adjustments That Allow Changing A Specified Number of ICE Layers Once minimum acceptable performance degradation has been established in association with a target ICE design, this information can be provided to an ICE fabrication system in which one or more ICEs are fabricated based on the target ICE design. Technologies for in-situ adjusting ICE fabrication by changing a specified total number of layers of the ICE to a new total number of layers are disclosed below to recover at least some of performance degradation of the ICE caused by errors associated with the ICE fabrication. A fabrication system for implementing these technologies is described first.

Figure 3:
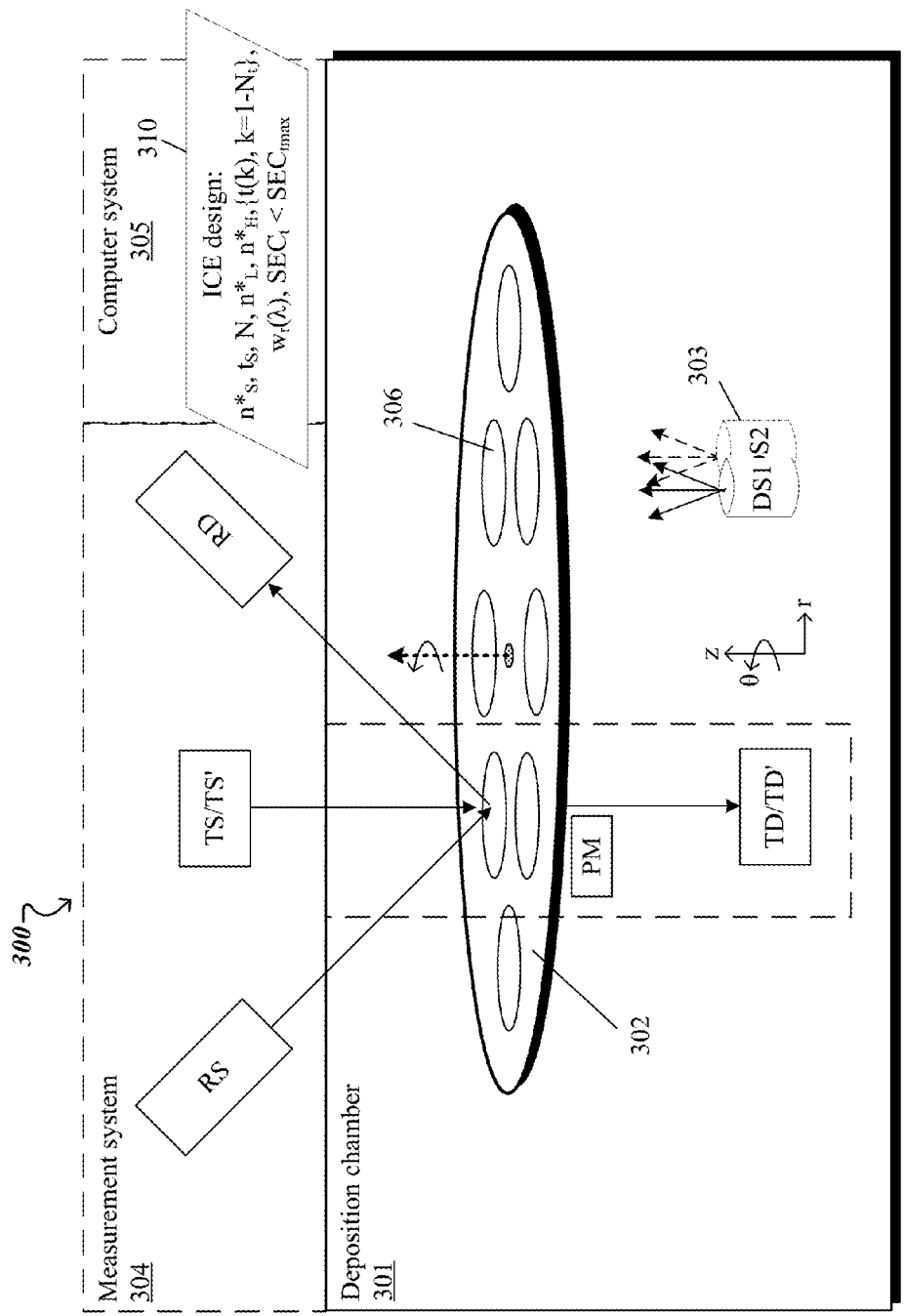
FIG. 3 shows an example of a system for fabricating one or more ICEs in which changing of a specified total number of layers of the ICEs to a new total number of layers is allowed during fabrication.

FIG. 3 shows a schematic representation of an example of an ICE fabrication system 300. The ICE fabrication system 300 includes a deposition chamber 301 to fabricate one or more ICEs 306, a measurement system 304 to measure at least one characteristic of the ICE while it is being fabricated, and a computer system 305 to control the fabrication of the one or more ICEs 306 based at least in part on results of the measurements.

The deposition chamber 301 includes one or more deposition sources 303 to provide materials with a low complex index of refraction $n^*_L$ and a high complex index of refraction $n^*_H$ used to form layers of the ICEs 306. Substrates on which layers of the ICEs 306 will be deposited are placed on a substrate support 302, such that the ICEs 306 are within the field of view of the deposition source(s) 303. The substrates have a thickness $t_S$ and a complex refractive index $n^*_S$ specified by the ICE design 307. Various physical vapor deposition (PVD) techniques can be used to form a stack of layers of each of the ICEs 306 in accordance with a target ICE design 145 or 245, for instance. In accordance with PVD techniques, the layers of the ICE(s) are formed by condensation of a vaporized form of material(s) of the source(s) 305, while maintaining vacuum in the deposition chamber 301. One such example of PVD technique is electron beam (E-beam) deposition, in which a beam of high energy electrons is electromagnetically focused onto material(s) of the deposition source(s) 303, e.g., either Si, or $SiO_2$, to evaporate atomic species. In some cases, E-beam deposition is assisted by ions, provided by ion-sources (not shown in FIG. 3), to clean or etch the ICE substrate(s); and/or to increase the energies of the evaporated material(s), such that they are deposited onto the substrates more densely, for instance. Other examples of PVD techniques that can be used to form the stack of layers of each of the ICEs 306 are cathodic arc deposition, in which an electric arc discharged at the material(s) of the deposition source(s) 303 blasts away some into ionized vapor to be deposited onto the ICEs 306 being formed; evaporative deposition, in which material(s) included in the deposition source(s) 303 is(are) heated to a high vapor pressure by electrically resistive heating; pulsed laser deposition, in which a laser ablates material(s) from the deposition source(s) 303 into a vapor; or sputter deposition, in which a glow plasma discharge (usually localized around the deposition source(s) 303 by a magnet—not shown in FIG. 3) bombards the material(s) of the source(s) 303 sputtering some away as a vapor for subsequent deposition.

A relative orientation of and separation between the deposition source(s) 303 and the substrate support 302 are configured to provide desired deposition rate(s) and spatial uniformity across the ICEs 306 disposed on the substrate support 302. Additionally, the substrate support 302 is rotated about the deposition chamber 301 (e.g., about the deposition chamber 301's azimuthal axis) and relative to the deposition source(s) 303 to obtain reproducibly uniform layer deposition of all the ICEs 306 within a batch.

In some implementations, the ICE fabrication system 300 can be used to deposit layers that are no thinner than a minimum thickness, $t_{min}$. Here, layers formed to a target thickness that is less than $t_{min}$ would have non-uniform thicknesses, for instance. The minimum thickness, $t_{min}$, represents an aspect of the deposition capability of the ICE fabrication system 300. Moreover, this aspect of the deposition capability can depend on material(s) of the source 303, type of source, relative distance and orientation between the source 303 and the substrate support 302, etc.

The measurement system 304 associated with the ICE fabrication system 300 includes one or more instruments. For example, a physical thickness monitor (e.g., a quartz crystal microbalance—not shown in FIG. 3) is used to measure a deposition rate, R. The measured deposition rate R is used to control power provided to the deposition source 303, its arrangement relative to the substrate support 302, etc. For instance, if an ICE design specifies that a $j^{th}$ layer L(j) of the N layers of an ICE is a Si layer with a target thickness t(j), a stack including the $(j-1)^{th}$ previously formed ICE layers is exposed to a Si source—from among the deposition sources 303—for a duration $\Delta T = t(j)/R_{Si}$, where the $R_{Si}$ is the measured deposition rate of the Si source. The measured deposition rate(s) R and the times used to deposit the formed layers L(1), L(2), . . . , L(j−1), L(j) can be used by the computer system 305 to determine actual values of the thicknesses t'(1), t'(2), . . . , t'(j−1), t'(j) of these layers.

Actual thicknesses and complex refractive indices of the formed layers L(1), L(2), . . . , L(j−1), L(j) also are determined by the computer system 305 from measurements of one or more characteristics of the formed layers. Throughout this specification, determining a complex refractive index n* of a layer means that both the real component Re(n*) and the imaginary component Im(n*) of the complex refractive index are being determined The characteristics of the formed layers are measured with other instruments of the measurement system 304.

For example, an ellipsometer is used to measure, after forming the $j^{th}$ layer of the ICE 306, amplitude and phase components $(\Psi(j), \Delta(j))$ of elliptically polarized probe light provided by source RS after reflection from the stack with j layers of the ICE that is being formed in the deposition chamber 301. Note that probe-light represents any type of electromagnetic radiation having one or more probe wavelengths from an appropriate region of the electromagnetic spectrum. In this case, the probe light is provided by the source RS through a probe window of the deposition chamber 301 associated with the ellipsometer, and the reflected light is collected by a detector RD through a detector window of the deposition chamber 301 associated with the ellipsometer. Here, the measured amplitude and phase components $(\Psi(j), \Delta(j))$ can be used by the computer system 305 to determine the complex refractive indices and thicknesses of each of the formed layers in the stack: $n^{*'}_{Si}$, $n^{*'}_{SiO2}$, t'(1), t'(2), . . . , t'(j−1), t'(j). The computer system 305 makes this determination by solving Maxwell's equations for propagating the interacted probe-light through the formed layers in the stack.

As another example, a spectrometer is used to measure, after forming the $j^{th}$ layer of the ICE 306, a spectrum $S(j;\lambda)$ of light provided by a source TS over a broad wavelength range from $\lambda_{min}$, $\lambda_{max}$ after transmission through the stack with j layers of the ICE that is being formed in the deposition chamber 301. In this case, the broad wavelength range source TS provides light through a probe window of the deposition chamber 301 associated with the spectrometer, and a detector TD collects the transmitted light through a detector window of the deposition chamber 301 associated with the spectrometer. Here, the measured spectrum $S(j;\lambda)$, over the wavelength range from $\lambda_{min},\lambda_{max}$, can be used by the computer system 305 to determine the complex refractive indices and thicknesses of each of the formed layers in the stack: $n^{*'}_{Si}$, $n^{*'}_{SiO2}$, t'(1), t'(2), . . . , t'(j−1), t'(j). The computer system 305 makes this determination by solving Maxwell's equations for propagating the interacted probe-light through the formed layers in the stack.

As yet another example, an optical monitor is used to measure, after forming the $j^{th}$ layer of the ICE 306, change of intensity $I(j;\lambda_k)$ of a probe light provided by source TS' due to transmission through the stack with j layers of the ICE that is being formed in the deposition chamber 301. The source of the optical monitor can be one and the same as the source of the spectrometer TS, which emits over a broad wavelength range, filtered with a filter centered on $\lambda_k$ having a narrow bandwidth $\Delta\lambda_k$, e.g., ±5 nm or less. Or the source of the optical monitor can be a different source TS' that emits one or more "discrete" wavelengths $\{\lambda_k, k=1, 2, \ldots\}$. A discrete wavelength $\lambda_k$ includes a center wavelength $\lambda_k$ within a narrow bandwidth $\Delta\lambda_k$, e.g., ±5 nm or less; two or more wavelengths, $\lambda_1$ and $\lambda_2$, contained in the probe-light have respective bandwidths $\Delta\lambda_1$ and $\Delta\lambda_2$ that are not overlapping. The source TS' can be a continuous wave (CW) laser, for instance. The source TS' provides, probe-light through a probe window of the deposition chamber 301 associated with the optical monitor and a detector TD' collects, through a detector window of the deposition chamber 301 associated with the optical monitor, the transmitted light with an intensity $I(j;\lambda_k)$. Here, the measured change of intensity $I(j;\lambda_k)$ can be used by the computer system 305 to determine the complex refractive indices and thicknesses of each of the formed layers in the stack: $n^{*'}_{Si}$, $n^{*'}_{SiO2}$, t'(1), t'(2), . . . , t'(j−1), t'(j). The computer system 305 makes this determination by solving Maxwell's equations for propagating the interacted probe-light through the formed layers in the stack.

The computer system 305 includes one or more hardware processors and memory. The memory encodes instructions that, when executed by the one or more hardware processors, cause the fabrication system 300 to perform processes for fabricating the ICEs 306. Examples of such processes are described below in connection with FIGS. 4 and 5. The computer system 305 also includes or is communicatively coupled with a storage system that stores one or more ICE designs 310, aspects of the deposition capability, and other information. The stored ICE designs can be organized in design libraries by a variety of criteria, such as ICE designs used to fabricate ICEs for determining values of a particular characteristic over many substances (e.g. the GOR ratio in crude oil, refined hydrocarbons, mud, etc.), or ICE designs used to fabricate ICEs for determining values of many properties of a given substance (e.g., viscosity, GOR, density, etc., of crude oil.) In this manner, upon receipt of an instruction to fabricate an ICE for measuring a given characteristic of a substance, the computer system 305 accesses such a design library and retrieves an appropriate ICE design 310 that is associated with the given characteristic of the substance.

The retrieved ICE design 307 includes specification of a substrate and a total number $N_t$ of layers to be formed in the deposition chamber 301 on the substrate; specification of a complex refractive index $n^*_S$ of a material of the substrate, a high complex refractive index $n^*_H$ and a low complex refractive index $n^*_L$ of materials (e.g., Si and $SiO_2$) to form the $N_t$ layers with adjacent layers having different complex refractive indices; and specification of target thicknesses $\{t_S, t(k), k=1–N_t\}$ of the substrate and the $N_t$ layers Implicitly or explicitly, the ICE design 307 also can include specification of a target optical spectrum $w_t(\lambda)$ associated with the given characteristic; and specification of a target $SEC_t$ representing expected performance of an ICE associated with the retrieved ICE design 307. The foregoing items of the retrieved ICE design 307 were determined, prior to fabricating the ICEs 306, in accordance with the ICE design process 200 described above in connection with FIG. 2. In some implementations, the ICE design 307 can include indication of maximum allowed $SEC_{max}$ caused by fabrication errors. Figures of merit other than the target $SEC_t$ can be included in the retrieved ICE design 307, e.g., SEP, the ICE sensitivity, etc.

The complex refractive indices and target thicknesses $\{t(k), k=1-N_t\}$ of the $N_t$ layers, as specified by the retrieved ICE design 310, are used by the computer system 305, in conjunction with aspects of deposition capability of the ICE fab system 300, to control deposition rate(s) of the deposition source(s) 303 and respective deposition times for forming the ICE layers. After the forming of each of the ICE layers, the computer system 305 instructs the measurement system 304 associated with the ICE fabrication system 300 to determined optical (e.g., complex refractive indices) and physical (e.g., thicknesses) characteristics of the formed layers. After forming, by the ICE fabrication system 300 in the foregoing manner, of one or more of the specified total number $N_t$ of layers, the computer system 350 may predict that a minimum performance degradation SEC of the ICE to be formed with the total number $N_t$ of layers—of which the formed layers have the determined complex refractive indices and thicknesses—exceeds the maximum allowed performance degradation $SEC_{max}$. In such case, the computer system 350 updates the retrieved ICE design 310 by (1) changing the specification of the total number $N_t$ of layers to a new total number $N'_t$ of layers and (2) obtaining new target layer thicknesses of layers remaining to be formed from the new total number $N'_t$ of layers, such that a predicted performance degradation SEC" of the ICE to be formed in accordance with the updated ICE design is at most equal to the maximum allowed performance degradation $SEC_{max}$. Then, the computer system 305 instructs the ICE fabrication system 300 to form one or more subsequent layers remaining to be formed from the new total number $N'_t$ of layers in accordance with the updated ICE design.

In some implementations, the specified total number $N_t$ of layers is increased to the new total number $N'_t$ of layers by one or more additional layers. Complex refractive indices of adjacent additional layers are different from each other and from the complex refractive indices of adjacent one or more of the layers remaining to be formed from the previously specified total number of layers. For example, if two additional layers are to be fabricated after the last layer $L(N)$ of the received ICE design, where a material of the last layer $L(N)$ is Si with complex refractive index $n^*_{Si}$, then a material of a first additional layer $L(N_t+1)$ is $SiO_2$ with complex refractive index $n^*_{SiO2}$, and a material of a second additional layer $L(N_t+2)$ is Si with complex refractive index $n^*_{Si}$. In some cases, when a material of the first additional layer $L(N_t+1)$ is different from $SiO_2$, e.g., $CaF_2$ with complex refractive index $n^*_{CaF2}$, then the material of the second additional layer $L(N_t+2)$ can be either $SiO_2$ with complex refractive index $n^*_{SiO2}$ or Si with complex refractive index $n^*_{Si}$. As another example, if two additional layers are to be fabricated between layers $L(k)$ and $L(k+1)$ of the received ICE design, where a material of the layer $L(k)$ is Si with complex refractive index $n^*_{Si}$ and a material of the layer $L(k+1)$ is $SiO_2$ with complex refractive index $n^*_{SiO2}$, then a material of a first additional layer $L(k+a)$ is $SiO_2$ with complex refractive index $n^*_{SiO2}$, and a material of a second additional layer $L(k+b)$ is Si with complex refractive index $n^*_{Si}$. Further, a material of the first additional layer $L(k+a)$ can be different from $SiO_2$, e.g., $CaF_2$ with complex refractive index $n^*_{CaF2}$, while the material of the second additional layer $L(k+b)$ is Si with complex refractive index $n^*_{Si}$, or a material of the second additional layer $L(k+b)$ can be different from Si, e.g., $CaF_2$ with complex refractive index $n^*_{CaF2}$, while the material of the first additional layer $L(k+a)$ is $SiO_2$ with complex refractive index $n^*_{SiO2}$. In this manner, the first additional layer $L(k+a)$ is formed between the layer $L(k)$ and the second additional layer $L(k+b)$, both of which have different complex refractive indices than the first additional layer $L(k+a)$. Similarly, the second additional layer $L(k+b)$ is formed between the first additional layer $L(k+a)$ and the layer $L(k+1)$, both of which have different complex refractive indices than the second additional layer $L(k+b)$.

In some implementations, the specified total number $N_t$ of layers is decreased to the new total number $N'_t$ of layers by one or more subtracted layers. For example, a pair of adjacent layers $L(k)$ and $L(k+1)$, where a material of the layer $L(k)$ is Si with complex refractive index $n^*_{Si}$ and a material of the layer $L(k+1)$ is $SiO_2$ with complex refractive index $n^*_{SiO2}$, can be subtracted from the retrieved ICE design 310, such that layers $L(k-1)$ and $L(k+2)$ become adjacent. In this manner, no design rule violation occurs when subtracting a pair of adjacent layers from the retrieved ICE design 310, because the newly adjacent layers have different complex refractive indices, namely a material of layer $L(k-1)$ is $SiO_2$ with complex refractive index $n^*_{SiO2}$ and a material of layer $L(k+2)$ is Si with complex refractive index $n^*_{Si}$. As another example, an odd or even number of layers can be subtracted from the retrieved ICE design 310, if the removed layers are, e.g., the last layer $L(N_t)$, the last two layers $L(N_t-1)$ and $L(N_t)$, the last three layers $L(N_t-2)$, $L(N_t-1)$ and $L(N_t)$, etc.

Figure 4:
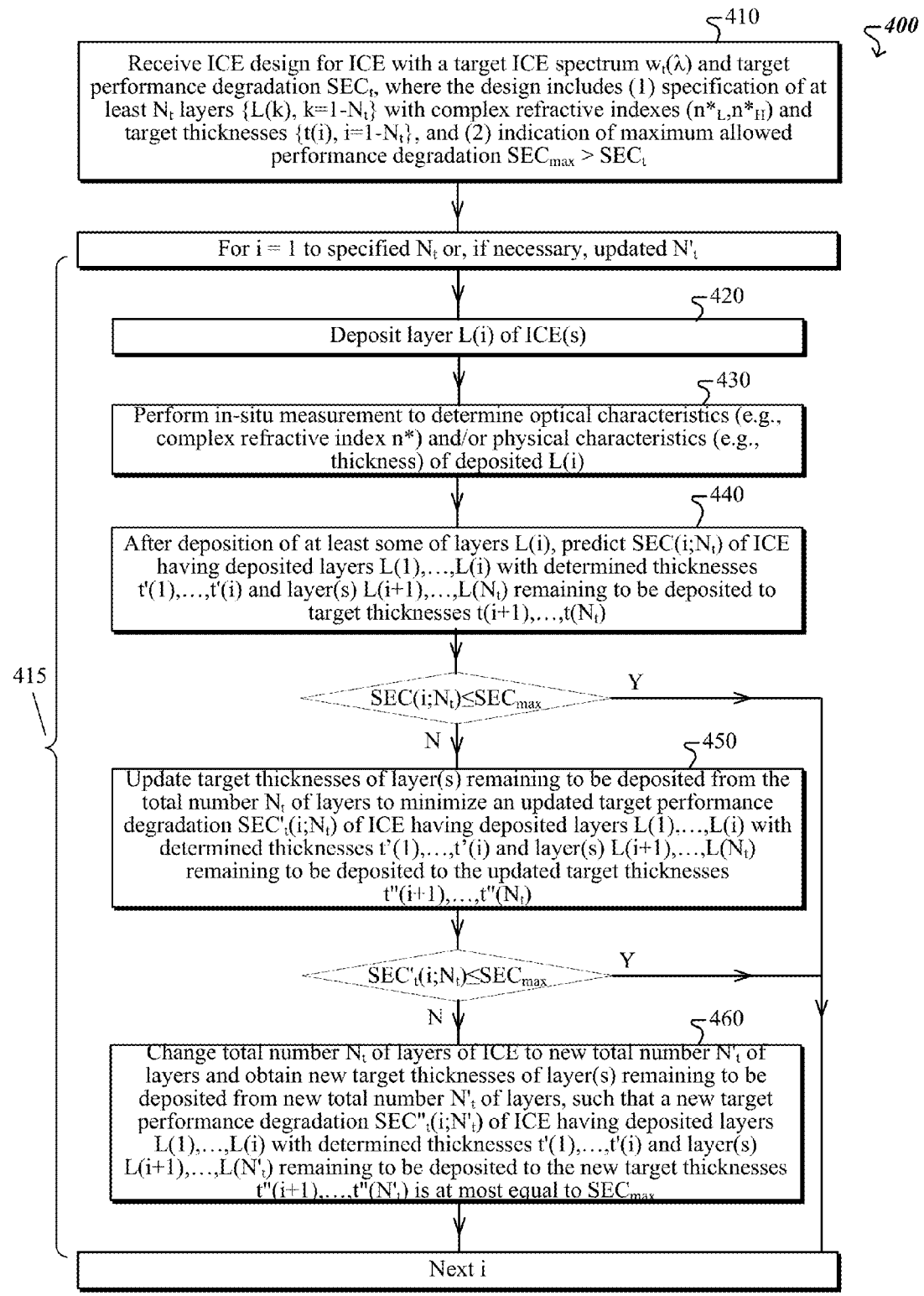
FIG. 4 is a flowchart showing an example of an ICE fabrication that allows changing of a specified total number of layers of the ICEs to a new total number of layers during the ICE fabrication.

(3.2) In-Situ Adjusting of ICE Fabrication By Changing A Specified Number of ICE Layers FIG. 4 is a flow chart of an example of an ICE fabrication process 400 for fabricating ICEs that allows for a specified total number of layers of the ICEs to be changed during fabrication to a new total number of layers to prevent performance of the fabricated ICEs from degrading under a threshold value. The process 400 can be implemented in conjunction with the ICE fabrication system 300 to adjust ICE fabrication. In such a context, the process 400 can be implemented as instructions encoded in the memory of the computer system 305, such that execution of the instructions, by the one or more hardware processors of the computer system 305, causes the ICE fabrication system 300 to perform the following operations.

At 410, an ICE design is received. The received ICE design includes specification of a substrate and $N_t$ layers $L(1), L(2), \ldots, L(N_t)$, each having a different complex refractive index from its adjacent layers, and specification of target complex refractive indices and thicknesses $t_S$, $t(1)$, $t(2), \ldots, t(N_t)$. In this manner, an ICE fabricated in accordance with the received ICE design selectively weights, when operated, light in at least a portion of a wavelength range by differing amounts. The differing amounts weighted over the wavelength range correspond to a target optical spectrum $w_t(\lambda)$ of the ICE and are related to a characteristic of a sample. For example, a design process for determining the specified (1) substrate and number $N_t$ of layers of the ICE, each having a different complex refractive index from its adjacent layers, and (2) complex refractive indices and thicknesses of the substrate and the $N_t$ layers that correspond to the target optical spectrum $w_t(\lambda)$ of the ICE is described above in connection with FIG. 2. In some implementations, the received ICE design also can include $SEC_t$ as an indication of a target performance of the ICE. The target performance represents an accuracy with which the ICE predicts, when operated, known values of the characteristic corresponding to validation spectra of the sample. Here, predicted values of the characteristic are obtained when the validation spectra weighted by the ICE are respectively integrated. Further, the received ICE design also includes indication of maximum allowed $SEC_{max}$ caused by fabrication errors.

Loop 415 is used to fabricate one or more ICEs based on the received ICE design. Each iteration "i" of the loop 415 is used to form a layer L(i) of a changed total number $N'_t$ of layers of the ICE or the specified total number $N_t$ of layers of the ICE, based on whether it is necessary or not to change the specified total number $N_t$ of layers of the ICE to prevent performance of the fabricated ICE from degrading under a threshold value.

At 420, the layer L(i) is formed to a target thickness t(i). The target thickness t(i) of the layer L(i) can be specified by the received ICE design or updated based on optimization(s) carried out after forming previous one or more of the layers of the ICE. In the example illustrated in FIG. 3, the deposition source 303 having a deposition rate R is used for a time duration $\Delta T(i)=t(i)/R$ to deposit the layer L(i) to its target thickness.

At 430, after the layer L(i) is formed, in-situ optical and/or physical measurements are performed to determine one or more characteristics of the formed layer L(i). In the example illustrated in FIG. 3, the in-situ optical measurements performed using the measurement system 304 include at least one of ellipsometry, spectroscopy and optical monitoring. In-situ physical measurements performed using the measurement system 304 include physical monitoring, e.g., with a crystal microbalance. Results of these in-situ optical and/or physical measurements are used to determine optical characteristics, e.g., complex refractive indices $n^{*'}_H$ and $n^{*'}_L$, and physical characteristics, e.g., thicknesses t'(1), t'(2), ..., t'(i-1), t'(i), of the formed layers: the layers L(1), L(2), ..., L(i-1) formed in previous iterations of the loop 415 and the just-completed layer L(i). If necessary, a deposition rate used to form the other layers L(i+1), L(i+2), ..., L($N_t$) remaining to be formed can be adjusted based on determined values of the complex refractive indices and thicknesses of the formed layers. Alternatively or additionally, complex refractive indices corresponding to the other layers L(i+1), L(i+2), ..., L($N_t$) remaining to be formed can be further adjusted based on the determined values of the complex refractive indices and thicknesses of the formed layers.

At 440, degradation in the ICE's performance SEC(i;$N_t$) relative to the target performance is predicted as if the ICE were completed to have the formed layers L(1), L(2), ..., L(i) with the determined thicknesses t'(1), t'(2), ..., t'(i), and the other layers L(i+1), L(i+2), ..., L($N_t$) remaining to be formed with target thicknesses t(i+1), t(i+2), ..., t($N_t$). In this case, the predicted performance degradation SEC(i;$N_t$) of the ICE is caused by deviations of the determined complex refractive indices and thicknesses of the formed layers from their respective complex refractive indices and target thicknesses specified by the current ICE design. If the predicted degradation in the ICE's performance SEC(i;$N_t$) is at most equal to the maximum allowed performance degradation $SEC_{max}$, SEC(i;$N_t$) ≤ $SEC_{max}$, then the next iteration of the loop 415 will be triggered to form the next layer L(i+1)—from the specified total number of layers $N_t$—to the target thickness t(i+1). If, however, the predicted degradation in the ICE's performance SEC(i;$N_t$) exceeds the maximum allowed performance degradation $SEC_{max}$, SEC(i;$N_t$) > $SEC_{max}$, then one or more optimizations are triggered. These optimizations are performed to recover some of the predicted performance degradation SEC(i;$N_t$).

At 450, target thicknesses of layers L(i), L(i+1), ..., L($N_t$) remaining to be formed are updated based on the determined complex refractive indices and thicknesses of the formed layers L(1), L(2), ..., L(i). This coarse optimization constrains the total number of layers of the ICE to the specified total number $N_t$ of layers and the thicknesses of the first layers L(1), L(2), ..., L(i) (which have been already formed) to the determined thicknesses t'(1), t'(2), ..., t'(i). In this manner, the coarse optimization obtains, in analogy with the process 200 described above in connection with FIG. 2, updated target thicknesses t"(i+1), t"(i+2), ..., t'($N_t$) of the other layers L(i+1), L(i+2), ..., L($N_t$) remaining to be formed, such that an updated target degradation of the ICE's performance SEC'$_t$(i;$N_t$) is minimum for the ICE having the first layers L(1), L(2), ..., L(i) formed with the determined thicknesses t'(1), t'(2), ..., t'(i), and the other layers L(i+1), L(i+2), ..., L($N_t$) remaining to be formed with the updated target thicknesses t"(i+1), t"(i+2), ..., t"($N_t$).

If the updated target degradation in the ICE's performance SEC'$_t$(i;$N_t$) is at most equal to the maximum allowed performance degradation $SEC_{max}$, SEC'$_t$(i;$N_t$) ≤ $SEC_{max}$, then the next iteration of the loop 415 will be triggered to form the next layer L(i+1) from the specified total number of layers $N_t$ to the updated target thickness t"(i+1). If, however, the updated target degradation in the ICE's performance SEC'$_t$(i;$N_t$) exceeds the maximum allowed performance degradation $SEC_{max}$, SEC'$_t$(i;$N_t$) > $SEC_{max}$, then another finer optimization is triggered to further recover some of the updated target performance degradation SEC'$_t$(i;$N_t$).

At 460, the specified total number of layers $N_t$ is changed to a new total number $N'_t$ of layers and target thicknesses of layer(s) L(i), L(i+1), ..., L($N'_t$) remaining to be formed from the new total number $N'_t$ of layers are obtained. This fine optimization changes the specified total number of layers $N_t$ multiple times, each time "j" by k(j) layers to an associated new total number $N'_t(j)=N_t+k(j)$, where k(j)=±1, ±2, ..., and j=1, 2, 3, 4, ... ; for each of the new total number of layers $N'_t(j)$, the fine optimization performs the process 200—described above in connection with FIG. 2—to obtain new target thicknesses t"(i+1;j), t"(i+2;j), ..., t"($N'_t(j)$) of the layers L(i+1), L(i+2), ..., L($N'_t(j)$) remaining to be formed, such that a new target degradation of the ICE's performance SEC"t(i;$N'_t(j)$) is minimum for an instance "j" of the ICE having the first layers L(1), L(2), ..., L(i) formed with the determined thicknesses t'(1), t'(2), ..., t'(i), and the other layers L(i+1), L(i+2), ..., L(N't(j)) remaining to be formed with the new target thicknesses t"(i+1), t"(i+2), ..., t"($N'_t(j)$).

For example, for a $1^{st}$ instance (j=1) of the ICE, the specified total number of layers $N_t$ is changed by subtracting one layer (k=−1) to obtain a $1^{st}$ new total number of layers $N'_t(1)=N_t−1$, and new target thicknesses t"(i+1;1), t"(i+2;1), ..., t"($N'_t(1)$) of the layers L(i+1), L(i+2), ..., L($N'_t(1)$) remaining to be formed are obtained that correspond to a $1^{st}$ minimum new target degradation of the ICE's performance SEC"t(i;$N'_t(1)$); for a $2^{nd}$ instance (j=2) of the ICE, the specified total number of layers $N_t$ is changed by adding one layer (k=+1) to obtain a $2^{nd}$ new total number of layers $N'_t(2)=N_t+1$, and new target thicknesses t"(i+1;2), t"(i+2;2), ..., t"($N'_t(2)$) of the layers L(i+1), L(i+2), ..., L($N'_t(2)$) remaining to be formed are obtained that correspond to a $2^{nd}$ minimum new target degradation of the ICE's performance SEC"t(i;$N'_t(2)$); for a $3^{rd}$ instance (j=3) of the ICE, the specified total number of layers $N_t$ is changed by subtracting two layers (k=−2) to obtain a $3^{rd}$ new total number of layers $N'_t(3)=N_t−2$, and new target thicknesses t"(i+1;3), t"(i+2;3), ..., t"($N'_t(3)$) of the layers L(i+1), L(i+2), . . . , L(N'$_t$(3)) remaining to be formed are obtained that correspond to a 3$^{rd}$ minimum new target degradation of the ICE's performance SEC"t(i;N'$_t$(3)); for a 4$^{th}$ instance (j=4) of the ICE, the specified total number of layers N$_t$ is changed by adding two layers (k=+2) to obtain a 4$^{th}$ new total number of layers N'$_t$(4)=N$_t$+2, then new target thicknesses t"(i+1;2), t"(i+2;2), . . . , t"(N'$_t$(4)) of the other layers L(i+1), L(i+2), . . . , L(N'$_t$(4)) remaining to be formed are obtained that correspond to a 4$^{th}$ minimum new target degradation of the ICE's performance SEC"$_t$(i;N'$_t$(4)); and so on. The set of new target performance degradations {SEC"$_t$(i;N'$_t$(1)), SEC"$_t$(i;N'$_t$(2)), SEC"$_t$(i;N'$_t$(3)), SEC"$_t$(i; N'$_t$(4)), . . . } are ranked and compared to the maximum allowed performance degradation SEC$_{max}$. The ones from the set of new target performance degradations that exceed the maximum allowed performance degradation SEC$_{max}$ are removed from further consideration.

The ICE design is updated based on a new target performance degradation from a subset of the new target performance degradations {SEC"$_t$(i;N'$_t$(p)), . . . , SEC"$_t$(i;N'$_t$(r)), all of which are at most equal to SEC$_{max}$} that corresponds to the minimum new total number N'$_t$=min{N'$_t$(p), . . . , N'$_t$(r)} of layers (or equivalently either to the maximum number of subtracted layers or the minimum number of additional layers). For example, if both SEC"$_t$(i;N$_t$+2) and SEC"$_t$(i;N$_t$+4) are at most equal to SEC$_{max}$, then the previous instance of the ICE design is updated with two additional layers (and not with four additional layers) to minimize the new total number of layers N'$_t$=N$_t$+2, or equivalently to minimize the number of layers to be added to the specified total number N$_t$ of layers. Here, the updated ICE design includes the layers L(1), L(2), . . . , L(i) formed with determined thicknesses t'(1), t'(2), . . . , t'(i), and other layers L(i+1), L(i+2), . . . , L(N$_t$), L(N$_t$+1), L(N$_t$+2) remaining to be formed with new target thicknesses t"(i+1), t"(i+2), . . . , t"(N$_t$), t"(N$_t$+1), t"(N$_t$+2) corresponding to the new target performance degradation SEC"$_t$(i;N$_t$+2). As another example, if both SEC"$_t$(i;N$_t$-2) and SEC"$_t$(i;N$_t$+2) are at most equal to SEC$_{max}$, then the previous instance of the ICE design is updated with two subtracted layers (and not with two additional layers) to minimize the new total number of layers N'$_t$=N$_t$-2, or equivalently to maximize the number of layers to be subtracted from the specified total number N$_t$ of layers. Here, the updated ICE design includes the layers L(1), L(2), . . . , L(i) formed with determined thicknesses t'(1), t'(2), . . . , t'(i), and other layers L(i+1), L(i+2), . . . , L(N$_t$-3), L(N$_t$-2) remaining to be formed with new target thicknesses t"(i+1), t"(i+2), . . . , t"(N$_t$-3), t"(N$_t$-2) corresponding to the new target performance degradation SEC"$_t$(i;N$_t$-2).

Once the previous instance of the ICE design is updated with specification of the new total number of layers N'$_t$ and the new target thicknesses t"(i+1), t"(i+2), . . . , t"(N'$_t$) which correspond to the new target performance degradation SEC"t(i;N'$_t$) and are used to form the remaining layers L(i+1), L(i+2), . . . , L(N'$_t$), the (i+1)$^{th}$ iteration from the N'$_t$ iterations of the loop 415 will be triggered to form the next layer L(i+1) from the new total number of layers N'$_t$ to the updated target thickness t"(i+1). In this manner, the remaining layers of the ICE will be formed based on the updated ICE design at least until another update is performed.

In some implementations, the predictive step 440—which may trigger coarse adjustments, at 450, and fine adjustments, at 460—is performed after forming each of the N$_t$ layers of the ICE as part of each respective iteration of the loop 415. In other implementations, the predictive step 440 is performed for the first time only after a predetermined number (or a predetermined fraction of the specified total number N$_t$) of layers is formed. For example, the predictive step 440 may be skipped after forming each of the first two layers of the ICE. As another example, the predictive step 440 is performed only after forming 50% (or 80%) of the specified total number N$_t$ of layers.

In some implementations, the predictive step 440 is performed repeatedly by skipping a number of formed layers. For example, the number of skipped layers is predetermined When the predetermined number is one, the predictive step 440—and if necessary one or both of the coarse update, at 450, and the fine update, at 460—is performed after forming each adjacent pair of Si-layer and SiO$_2$-layer. Here, the predictive step 440 is skipped after forming the odd layers and is performed only after forming the even layers of the ICE, for instance. As another example, the number of skipped layers is random. For instance, a first prediction can be made, at 440, after forming the 2$^{nd}$ layer L(2), a second prediction can be made, at 440, after forming the 8$^{th}$ layer L(8), a third prediction can be made, at 440, after forming the 11$^{th}$ layer L(11), a fourth prediction can be made, at 440, after forming the 19$^{th}$ layer L(19), and so on. Here, the predictive step 440 is skipped after forming each of the layers between the noted layers.

An example of adjusting ICE fabrication by adding, during the ICE fabrication, extra layers to a specified total number of layers of an ICE design to prevent performance of the fabricated ICEs from degrading under a threshold value is described below.

EXAMPLE

Figure 5:
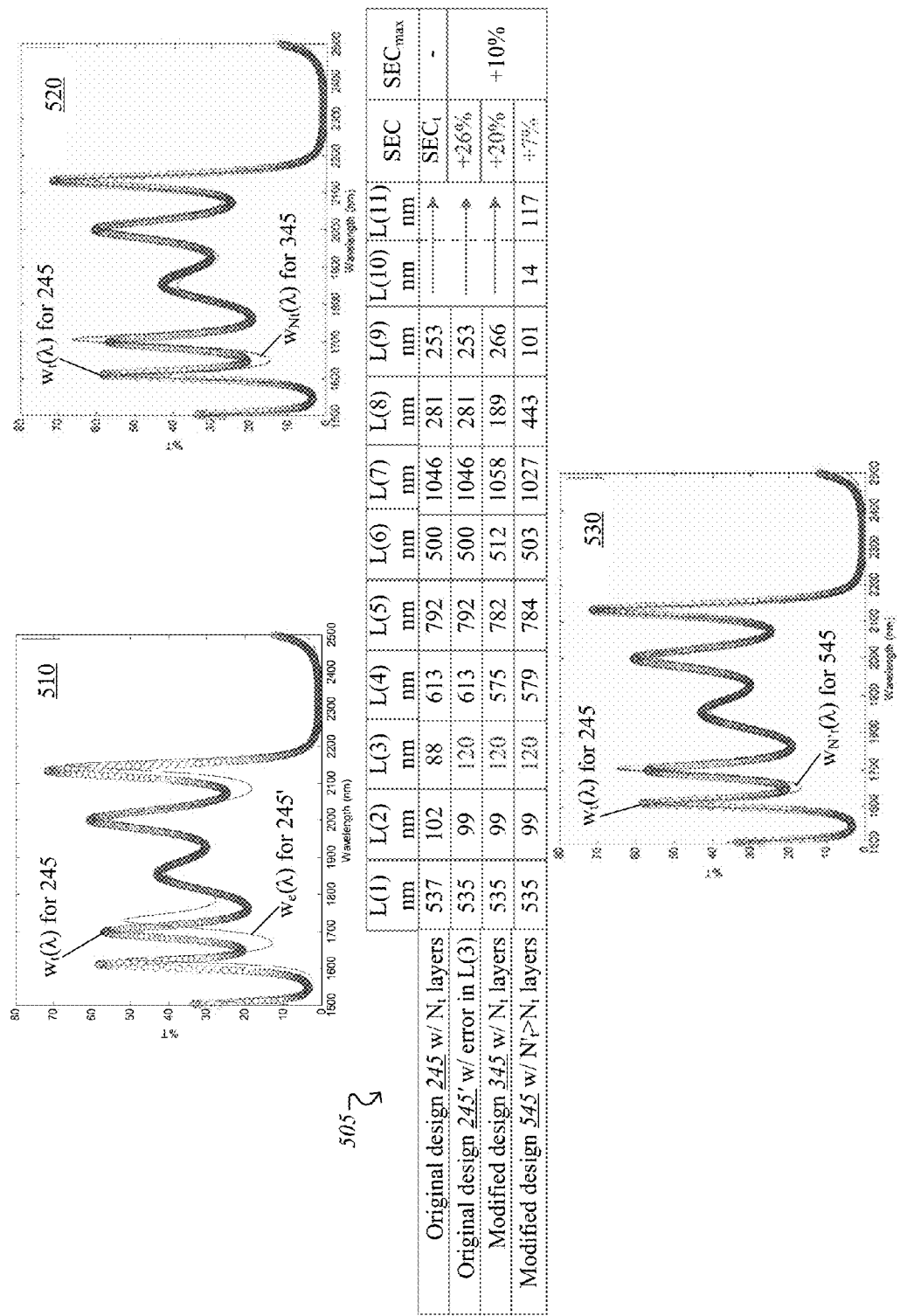
FIG. 5 shows aspects of the ICE fabrication described in FIG. 4.

FIG. 5 shows aspects of forming, in accordance with the process 400, layer L(3) of the ICE design 245 described above in connection with FIG. 2.

The ICE design 245—here referred to as the original ICE design—specifies 9 total layers (N$_t$=9) having alternating complex indices of refraction (n*$_{Si}$, n*$_{SiO2}$). Target thicknesses t(1), t(2), t(9) specified by the original ICE design 245 are reproduced in the first line of Table 505. A target optical spectrum w$_t$(λ) corresponding to the target thicknesses specified by the original ICE design 245 is represented in each of graphs 510, 520 and 530 using open circles. An expected degradation of performance of an ICE associated with the original ICE design 245 is quantified in terms of a target SEC$_t$, as described above in connection with FIG. 2. The value of the target SEC$_t$ (reproduced in Table 505 at the intersection of the first row with the column labeled "SEC") is expressed in measurement units of a characteristic (here GOR) to which the target optical spectrum w$_t$(λ) relates. Additionally, the last column of Table 505 indicates a maximum acceptable degradation of the ICE's performance SEC$_{max}$. The SEC$_{max}$ can be provided as an absolute value (using the same measurement units used for the target SEC$_t$) or as a relative (dimensionless) fraction "f" of the target SEC$_t$, f=(SEC$_{max}$-SEC$_t$)/SEC$_t$. In the example illustrated in FIG. 5, f=10%, so performance degradation that exceeds the target performance degradation SEC$_t$ by more than 10% is unacceptable, while performance degradation that exceeds the target performance degradation SEC$_t$ by less than 10% is acceptable.

Results obtained prior to and during the 3$^{rd}$ iteration of the process 400 are shown in the remaining rows of Table 505.

For instance, a 1$^{st}$ layer L(1) and a 2$^{nd}$ layer L(2) were respectively formed in accordance with 1$^{st}$ and 2$^{nd}$ iterations of the process 400, and their thicknesses were respectively determined to be t'(1) and t'(2). As part of the 3$^{rd}$ iteration of the process 400, a 3$^{rd}$ layer L(3) was formed, at 420, and a thickness t'(3) of the formed layer L(3) was determined, at 430. The determined thicknesses t'(1), t'(2) and t'(3) of the formed layers L(1), L(2) and L(3), and the target thicknesses t(4), t(5), t(6), t(7), t(8) and t(9) of the layers L(4), L(5), L(6), L(7), L(8) and L(9) remaining to be formed are shown in the second row of Table 505. Note that the determined thicknesses t'(1) and t'(2) of the first two formed layers L(1) and L(2) differ insignificantly (by less than 0.4% and 3%, respectively) from their target thicknesses t(1) and t(2). As such, no updates were made, prior to the 3$^{rd}$ iteration, to target thicknesses of the layers remaining to be formed. Also note that the determined thickness t'(3) of the third formed layer L(3) differs significantly (by about 37%) from its target thickness t(3). A optical spectrum $w_e(\lambda)$—corresponding to the determined thicknesses t'(1), t'(2) and t'(3) of the formed layers L(1), L(2) and L(3), and the target thicknesses t(4), t(5), t(6), t(7), t(8) and t(9) of the layers L(4), L(5), L(6), L(7), L(8) and L(9) remaining to be formed—is represented in Graph 510, using solid line, along with the target optical spectrum $w_t(\lambda)$. Spectral differences (quantified as RMS, for instance) between the optical spectrum $w_e(\lambda)$ and the target optical spectrum $w_t(\lambda)$ are induced by the errors in forming the first three layers L(1), L(2), L(3) and can lead to further performance degradation of the target performance degradation $SEC_t$. As expected, a predicted performance degradation SEC(3;9)—calculated at 440 of the 3$^{rd}$ iteration based on the thicknesses shown in the second row of Table 505—is 26% larger than the target performance degradation $SEC_t$. Hence, the predicted performance degradation SEC(3;9) is 16% larger than the maximum acceptable performance degradation $SEC_{max}$.

For this reason, a coarse optimization—which maintains the total number of layers of the ICE design to 9—is performed at 450 of the 3$^{rd}$ iteration of the process 400. The coarse optimization updates the target thicknesses of the layers L(4), L(5), L(6), L(7), L(8) and L(9) remaining to be formed to minimize an updated target performance degradation $SEC_t(3;9)$. The determined thicknesses t'(1), t'(2) and t'(3) of the formed layers L(1), L(2) and L(3), the updated target thicknesses t'(4), t"(5), t"(6), t"(7), t"(8) and t"(9) of the layers L(4), L(5), L(6), L(7), L(8) and L(9) remaining to be formed, and the updated target $SEC'_t(3;9)$ are shown in the third row of Table 505. An optical spectrum $w_{N't}(\lambda)$ corresponding to the thicknesses in the third row of Table 505 is represented in Graph 520, using solid line, along with the target optical spectrum $w_t(\lambda)$. In Graph 520, spectral differences between the optical spectrum $w_{N't}(\lambda)$ and the target optical spectrum $w_t(\lambda)$ are smaller than the spectral differences between the optical spectrum $w_e(\lambda)$ and the target optical spectrum $w_t(\lambda)$ shown in Graph 510. Although smaller than prior to the coarse optimization, these spectral differences still cause the minimized target performance degradation $SEC'_t(3;9)$ to be 20% larger than the target performance degradation $SEC_t$. Hence, the minimized target performance degradation $SEC'_t(3;9)$ is 10% larger than the maximum acceptable performance degradation $SEC_{max}$.

For this reason, a fine optimization—which changes the total number of layers of the ICE design from 9—is performed at 460 of the 3$^{rd}$ iteration of the process 400. In the example illustrated in FIG. 5, the fine optimization increases the total number of layers from 9 by two additional layers L(10) and L(11) to a new total number of layers $N'_t=11$. In this manner, new target thicknesses t"(4), t"(5), t"(6), t"(7), t"(8), t"(9), t"(10) and t"(11) are obtained for the layers L(4), L(5), L(6), L(7), L(8), L(9) of the original ICE design 245 and the two additional layers L(10), L(11) remaining to be formed, such that a new target performance degradation $SEC"_t(3;11)$ is at most equal to the maximum acceptable degradation $SEC_{max}$. The determined thicknesses t'(1), t'(2) and t'(3) of the formed layers L(1), L(2) and L(3), the new target thicknesses t"(4), t"(5), t"(6), t"(7), t"(8), t"(9), t"(10) and t"(11) of the layers L(4), L(5), L(6), L(7), L(8), L(9) of the original ICE design 245 and the two additional layers L(10), L(11) remaining to be formed, and the new target performance degradation $SEC"_t(3;11)$ are shown in the fourth row of Table 505. An optical spectrum $w_{N't}(\lambda)$ corresponding to the thicknesses in the fourth row of Table 505 is represented in Graph 530, using solid line, along with the target optical spectrum $w_t(\lambda)$. In Graph 530, spectral differences between the optical spectrum $w_{N't}(\lambda)$ and the target optical spectrum $w_t(\lambda)$ are smaller than the spectral differences between the optical spectrum $w_{N't}(\lambda)$ and the target optical spectrum $w_t(\lambda)$ shown in Graph 520. Such improved spectral matching between the optical spectrum $w_{N't}(\lambda)$ of the updated ICE design with 11 total layers and the target optical spectrum $w_t(\lambda)$ of the original ICE design with 9 total layers causes the new target performance degradation $SEC"_t(3;11)$ to be only 7% larger than the target performance degradation $SEC_t$. As the new target performance degradation $SEC"_t(3;11)$ is 3% smaller than the maximum acceptable performance degradation $SEC_{max}$, the 3$^{rd}$ iteration of the process 400 can be completed.

Hence, the 4$^{th}$ iteration of the process 400 will be performed next to form the 4$^{th}$ layer L(4) out of 11 total layers of the updated ICE design to a new target thickness of t"(4).

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. A method performed by a fabrication system, the method comprising:
  receiving a design of an integrated computational element (ICE), the ICE design comprising:
  specification of a substrate and a plurality of layers, their respective target thicknesses and complex refractive indices, wherein complex refractive indices of adjacent layers are different from each other, and wherein a notional ICE fabricated in accordance with the ICE design is related to a characteristic of a sample, and indication of maximum allowed performance degradation of the notional ICE's performance relative to a target performance caused by fabrication errors;

forming one or more of the layers of an ICE in accordance with the ICE design;

determining that a minimum performance degradation of the ICE would exceed the maximum allowed degradation if the ICE having the formed one or more layers were to be completed based on the received ICE design;

updating, in response to said determining, the ICE design by changing a previously specified total number of layers to a new total number of layers and obtaining new target layer thicknesses and complex refractive indices of layers remaining to be formed from the new total number of layers, such that a performance degradation of the ICE to be completed based on the updated ICE design is at most equal to the maximum allowed performance degradation; and forming one or more subsequent layers remaining to be formed from the new total number of layers in accordance with the updated ICE design.

2. The method of claim 1, wherein said changing the specification of the total number of layers to the new total number of layers comprises increasing the previously specified total number of layers by one or more additional layers, and complex refractive indices of adjacent ones of the additional layers are different from each other and from the complex refractive indices of adjacent one or more of the layers remaining to be formed from the previously specified total number of layers.

3. The method of claim 2, wherein said increasing the total number of layers by one or more additional layers comprises indicating that the one or more additional layers be formed after originally specified total number of layers are formed.

4. The method of claim 2, wherein said increasing the total number of layers by one or more additional layers comprises increasing the total number of layers by two or more additional layers.

5. The method of claim 4, wherein originally specified complex refractive indices are first and second complex refractive indices, and at least one of the two or more additional layers has a third complex refractive index different from the first or second complex refractive indices.

6. The method of claim 2, wherein if said increasing the number of previously specified total number of layers by either a first number of additional layers or a second number of additional layers, different from the first number, causes the performance degradation of the ICE to not exceed the maximum performance degradation, then the previously specified total number of layers is increased by the smaller of the first or second number of additional layers.

7. The method of claim 1, said changing the specification of the total number of layers to the new total number of layers comprises decreasing the previously specified total number of layers by one or more subtracted layers.

8. The method of claim 7, wherein the one or more subtracted layers comprise two adjacent layers having different complex refractive indices.

9. The method of claim 7, wherein if said decreasing the number of previously specified total number of layers by either a first number of subtracted layers or a second number of subtracted layers, different from the first number, causes the performance degradation of the ICE to not exceed the maximum performance degradation, then the previously specified total number of layers is decreased by the larger of the first or second number of subtracted layers.

10. The method of claim 1, wherein at least a predetermined fraction of the total number of layers is formed prior to performing said determining and said updating.

11. The method of claim 10, wherein the predetermined fraction is 20-80%.

12. The method of claim 1, wherein said determining and said updating are performed repeatedly by skipping a predetermined number of formed layers.

13. The method of claim 12, wherein the predetermined number of formed layers is two.

14. The method of claim 1, wherein said determining and said updating are performed repeatedly by skipping a random number of formed layers.

15. The method of claim 1, wherein said determining and said updating are performed after forming each of the layers of the ICE.

16. The method of claim 1, wherein said determining that the minimum performance degradation would exceed the maximum allowed degradation comprises determining one or more of complex refractive index and thickness associated with each of the one or more formed layers.

17. The method of claim 16, wherein said determining the complex refractive index and thickness associated with each of the one or more formed layers comprises performing ellipsometry of the formed layers.

18. The method of claim 16, wherein said determining the complex refractive index and thickness associated with each of the one or more formed layers comprises optical monitoring of the formed layers.

19. The method of claim 16, wherein said determining the complex refractive index and thickness associated with each of the one or more formed layers comprises performing spectroscopy of the formed layers.

20. The method of claim 16, wherein said determining the thickness associated with each of the one or more formed layers comprises performing physical monitoring of the formed layers.

21. The method of claim 16, further comprising updating a deposition rate or time used to form the layers remaining to be formed based on the complex refractive indices and thicknesses of the formed layers.

22. The method of claim 16, further comprising modifying complex refractive indices corresponding to the layers remaining to be formed based on the complex refractive indices and thicknesses of the formed layers.

23. The method of claim 1, wherein a metric of degradation of the notional ICE's performance is a standard error of calibration (SEC).

24. A system comprising:

a deposition chamber;

one or more deposition sources associated with the deposition chamber to provide materials from which layers of one or more integrated computational elements (ICEs) are formed;

one or more supports disposed inside the deposition chamber, at least partially, within a field of view of the one or more deposition sources to support the layers of the ICEs while the layers are formed;

a measurement system associated with the deposition chamber to measure one or more characteristics of the layers while the layers are formed; and a computer system in communication with at least some of the one or more deposition sources, the one or more supports and the measurement system, wherein the computer system comprises one or more hardware processors and non-transitory computer-readable medium encoding instructions that, when executed by the one or more hardware processors, cause the system to form the layers of the ICEs by performing operations comprising:

receiving an ICE design of the ICEs, the ICE design comprising specification of a substrate and a plurality of layers, their respective target thicknesses and complex refractive indices, wherein complex refractive indices of adjacent layers are different from each other, and wherein a notional ICE fabricated in accordance with the ICE design is related to a characteristic of a sample, and indication of maximum allowed performance degradation of the notional ICE's performance relative to a target performance caused by fabrication errors;

forming one or more of the layers of the ICEs in accordance with the ICE design;

determining that a minimum performance degradation of the ICEs would exceed the maximum allowed degradation if the ICEs having the formed one or more layers were to be completed based on the received ICE design;

updating, in response to said determining, the ICE design by changing a previously specified total number of layers to a new total number of layers and obtaining new target layer thicknesses and complex refractive indices of layers remaining to be formed from the new total number of layers, such that a performance degradation of the ICEs to be completed based on the updated ICE design is at most equal to the maximum allowed performance degradation; and forming one or more subsequent layers remaining to be formed from the new total number of layers in accordance with the updated ICE design.

25. The system of claim 24, wherein the measurement system comprises an ellipsometer.

26. The system of claim 24, wherein the measurement system comprises an optical monitor.

27. The system of claim 24, wherein the measurement system comprises a spectrometer.

28. The system of claim 24, wherein the measurement system comprises an optical monitor including a crystal microbalance.

* * * * *